(12) United States Patent
Ong et al.

(10) Patent No.: US 8,808,693 B2
(45) Date of Patent: Aug. 19, 2014

(54) SEMAPHORIN 3C (SEMA3C) INHIBITOR THERAPEUTICS, METHODS, AND USES

(75) Inventors: Christopher J. Ong, Vancouver (CA); Martin E. Gleave, Vancouver (CA); Norihiro Hayashi, Vancouver (CA); James Peacock, Vancouver (CA)

(73) Assignee: The University of British Columbia, Vancouver (CA)

( * ) Notice: Subject to any disclaimer, the term of this patent is extended or adjusted under 35 U.S.C. 154(b) by 47 days.

(21) Appl. No.: 13/262,196

(22) PCT Filed: Apr. 1, 2010

(86) PCT No.: PCT/CA2010/000514
§ 371 (c)(1),
(2), (4) Date: Jan. 3, 2012

(87) PCT Pub. No.: WO2010/111792
PCT Pub. Date: Oct. 7, 2010

(65) Prior Publication Data
US 2013/0028896 A1    Jan. 31, 2013

Related U.S. Application Data

(60) Provisional application No. 61/202,756, filed on Apr. 1, 2009.

(51) Int. Cl.
*A61K 39/395* (2006.01)
*A61K 39/00* (2006.01)

(52) U.S. Cl.
USPC .................. 424/130.1; 424/135.1; 424/141.1

(58) Field of Classification Search
CPC .................. A61K 39/39533; A61K 39/39558; A61K 2039/55; C07K 2316/96; C07K 16/18; C07K 16/28
See application file for complete search history.

(56) References Cited

U.S. PATENT DOCUMENTS

| | | | |
|---|---|---|---|
| 5,981,222 A | 11/1999 | Jacobs et al. | |
| 7,045,605 B2* | 5/2006 | Bander et al. | 530/388.8 |
| 2005/0244851 A1 | 11/2005 | Blume et al. | |
| 2007/0161016 A1* | 7/2007 | Afar et al. | 435/6 |

FOREIGN PATENT DOCUMENTS

WO    03009814    2/2003

OTHER PUBLICATIONS

Lu et al., The AAPS Journal 2006, 8(3): E466-E478.*
Mendoza., Arch. Immunol. Ther. Exp., vol. 53, p. 47-60, 2005.*
Banu et al. (2006) "Smaphorin 3C Regulates Endothelial Cell Function by Increasing Integrin Activity" FASEB J. 20 (12):E1520-E1527.
Chung (2007) "Semaphorin Signaling Facilitates Cleft Formation in the Developing Salivary Gland" Development 134 (16):2935-2945.
Herman & Meadows (2007) "Increased Class 3 Semaphorin Expression Modulates the invasive and Adhesive Properties of Prostate Cells" Int. J. Oncology 30(5):1231-1238.
Miyamoto et al. (2004) "Androgen Deprivation Therapy for Prostate Cancer: Current Status and Future Prospects" Prostate 61(4):332-353.
Zimmer et al. (2008) "Small-Molecule Inhibitors of HIF-2a Translation link its 5'UTR Iron-Responsive Element to Oxygen Sensing" Mol. Cell 32(6):838-848.
Database NCBI Entrez + Accession #Q62181 SEMA 3C Mouse May 30, 2000.
Database NCBI Entrez + Accession #Q99985.2 SEMA 3c Human May 30, 2000.
Giordano, S., et al., (2002) "The Semaphorin 4D receptor controls invasive growth by coupling with Met" Nat Cell Biol 4 (9):720-724.
Hayashi, N. et al. (2006) "Clustrin May Regulate NF-KBeta-regulated Genes" Journal of Urology, 175(4):84-85.
Heinlein, C.A. and Chang C., (2004) "Androgen Receptor in Prostate Cancer" Endocrine Reviews, 25(2): 276-308.
Huggins and Hodges, (1941) "The Effect of Castration, of Estrogen and of Androgen Injection on Serum Phosphatases in Metastatic Carcinoma of the Prostate" Cancer Research, 1:293-297.
Kolodkin, A.L., (1993) "The Semaphorin Genes Encode a Family of Transmembrane and Secreted Growth Cone Guidance Molecules." Cell, 75(7):1389-1399.
Kruger, R.P., et al., (2005)."Semaphorins Command Cells to Move." Nat Rev Mol Cell Biol, 6(10):789-800.
Lecerf et al., (2001) "Human single-chain Fv intrabodies counteract in situ huntingtin aggregation in cellular models of Huntington's disease" PNAS, 98(8):4764-4769.
Negishi, M., I. Oinuma, and H. Katoh, (2005) "Plexins: axon guidance and signal transduction" Cell Mol Life Sci, 62:1363-1371.
Pan, W.H. and G.A. Clawson, (2006) "Identifying Accessible Sites in RNA: The First Step in Designing Antisense Reagents" Curr Med Chem, 13(25):3083-3103.
Patzel, V., (2007). "In silico selection of active siRNA" Drug Discovery Today, 12(304):139-148.
Peek, A.S. and M.A. Behlke, (2007) "Design of active small interfering RNAs" Curr Opin Mol Ther, 9(2): 110-118.
Petrylak, et al., (2004) "Docetaxel and Estramustine Compared with Mitoxantrone and Prednisone for Advanced Refractory Prostate Cancer" NEJM, 351:1513-1520.
Rizzolio, S. and Tamagnone, L., (2007) "Semaphorin Signals on the Road to Cancer Invasion and Metastasis" Cell Adhesion and Migration, 1 (2):62-68.
Swiercz, J.M., et al., (2004) "Plexin-B1/RhoGEF-mediated RhoA activation involves the receptor tyrosine kinase ErbB-2" J Cell Biol, 165(6):869-880.

(Continued)

*Primary Examiner* — Hong Sang
(74) *Attorney, Agent, or Firm* — Carol L. Francis; Bozicevic, Field & Francis LLP

(57) ABSTRACT

Provided are methods, uses and pharmaceutical compositions for treatment of prostate cancer with a SEMA3C inhibitor in a biologically effective amount sufficient to cause cell death of a prostate cancer cell or to inhibit proliferation of the prostate cancer cells. The prostate cancer may be an androgen receptor (AR) positive prostate cancer and the SEMA3C inhibitor may be selected from one or more of the following: an antibody, a SEMA3C peptide, an antisense RNA, a siRNA, a shRNA or a small molecule.

15 Claims, 16 Drawing Sheets

(56) References Cited

OTHER PUBLICATIONS

Swiercz, J.M., et al., (2008) "ErbB-2 and met reciprocally regulate cellular signaling via plexin-B1" J Biol Chem, 283(4):1893-1901.
Tamagnone, L. and P.M. Comoglio, (2000) "Signalling by semaphorin receptors: cell guidance and beyond" Trends Cell Biol, 10(9):377-383.
Tannock et al., (2004) "Docetaxel plus Prednisone or Mitoxantrone plus Prednisone for Advanced Prostate Cancer" NEJM, 351:1502-1512.
Verras, M., et al., (2007) "The Androgen Receptor Negatively Regulates the Expression of c-Met: Implications for a Novel Mechanism of Prostate Cancer Progression" Cancer Res, 67(3): 967-975.

* cited by examiner

A

B

SEQUENCE LISTING

<160> NUMBER OF SEQ ID NOS: 119

<210> SEQ ID NO 1
<211> LENGTH: 751
<212> TYPE: PRT
<213> ORGANISM: homo sapiens

<400> SEQUENCE: 1

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
            20                  25                  30

Phe Asp Glu Leu Arg Glu Thr Lys Thr Ser Glu Tyr Phe Ser Leu Ser
        35                  40                  45

His His Pro Leu Asp Tyr Arg Ile Leu Leu Met Asp Glu Asp Gln Asp
    50                  55                  60

Arg Ile Tyr Val Gly Ser Lys Asp His Ile Leu Ser Leu Asn Ile Asn
65                  70                  75                  80

```
Asn Ile Ser Gln Glu Ala Leu Ser Val Phe Trp Pro Ala Ser Thr Ile
                85                  90                  95
Lys Val Glu Glu Cys Lys Met Ala Gly Lys Asp Pro Thr His Gly Cys
            100                 105                 110
Gly Asn Phe Val Arg Val Ile Gln Thr Phe Asn Arg Thr His Leu Tyr
        115                 120                 125
Val Cys Gly Ser Gly Ala Phe Ser Pro Val Cys Thr Tyr Leu Asn Arg
    130                 135                 140
Gly Arg Arg Ser Glu Asp Gln Val Phe Met Ile Asp Ser Lys Cys Glu
145                 150                 155                 160
Ser Gly Lys Gly Arg Cys Ser Phe Asn Pro Asn Val Asn Thr Val Ser
                165                 170                 175
Val Met Ile Asn Glu Glu Leu Phe Ser Gly Met Tyr Ile Asp Phe Met
            180                 185                 190
Gly Thr Asp Ala Ala Ile Phe Arg Ser Leu Thr Lys Arg Asn Ala Val
        195                 200                 205
Arg Thr Asp Gln His Asn Ser Lys Trp Leu Ser Glu Pro Met Phe Val
    210                 215                 220
Asp Ala His Val Ile Pro Asp Gly Thr Asp Pro Asn Asp Ala Lys Val
225                 230                 235                 240
Tyr Phe Phe Phe Lys Glu Lys Leu Thr Asp Asn Asn Arg Ser Thr Lys
                245                 250                 255
Gln Ile His Ser Met Ile Ala Arg Ile Cys Pro Asn Asp Thr Gly Gly
            260                 265                 270
Leu Arg Ser Leu Val Asn Lys Trp Thr Thr Phe Leu Lys Ala Arg Leu
        275                 280                 285
Val Cys Ser Val Thr Asp Glu Asp Gly Pro Glu Thr His Phe Asp Glu
    290                 295                 300
Leu Glu Asp Val Phe Leu Leu Glu Thr Asp Asn Pro Arg Thr Thr Leu
305                 310                 315                 320
Val Tyr Gly Ile Phe Thr Thr Ser Ser Ser Val Phe Lys Gly Ser Ala
                325                 330                 335
Val Cys Val Tyr His Leu Ser Asp Ile Gln Thr Val Phe Asn Gly Pro
            340                 345                 350
Phe Ala His Lys Glu Gly Pro Asn His Gln Leu Ile Ser Tyr Gln Gly
        355                 360                 365
Arg Ile Pro Tyr Pro Arg Pro Gly Thr Cys Pro Gly Gly Ala Phe Thr
    370                 375                 380
Pro Asn Met Arg Thr Thr Lys Glu Phe Pro Asp Asp Val Val Thr Phe
385                 390                 395                 400
Ile Arg Asn His Pro Leu Met Tyr Asn Ser Ile Tyr Pro Ile His Lys
                405                 410                 415
Arg Pro Leu Ile Val Arg Ile Gly Thr Asp Tyr Lys Tyr Thr Lys Ile
            420                 425                 430
Ala Val Asp Arg Val Asn Ala Ala Asp Gly Arg Tyr His Val Leu Phe
        435                 440                 445
Leu Gly Thr Asp Arg Gly Thr Val Gln Lys Val Val Leu Pro Thr
    450                 455                 460
Asn Asn Ser Val Ser Gly Glu Leu Ile Leu Glu Glu Leu Glu Val Phe
465                 470                 475                 480
Lys Asn His Ala Pro Ile Thr Thr Met Lys Ile Ser Ser Lys Lys Gln
                485                 490                 495
```

```
Gln Leu Tyr Val Ser Ser Asn Glu Gly Val Ser Gln Val Ser Leu His
                500                 505                 510

Arg Cys His Ile Tyr Gly Thr Ala Cys Ala Asp Cys Cys Leu Ala Arg
            515                 520                 525

Asp Pro Tyr Cys Ala Trp Asp Gly His Ser Cys Ser Arg Phe Tyr Pro
        530                 535                 540

Thr Gly Lys Arg Ser Arg Arg Gln Asp Val Arg His Gly Asn Pro
545                 550                 555                 560

Leu Thr Gln Cys Arg Gly Phe Asn Leu Lys Ala Tyr Arg Asn Ala Ala
                565                 570                 575

Glu Ile Val Gln Tyr Gly Val Lys Asn Asn Thr Thr Phe Leu Glu Cys
            580                 585                 590

Ala Pro Lys Ser Pro Gln Ala Ser Ile Lys Trp Leu Leu Gln Lys Asp
        595                 600                 605

Lys Asp Arg Arg Lys Glu Val Lys Leu Asn Glu Arg Ile Ile Ala Thr
    610                 615                 620

Ser Gln Gly Leu Leu Ile Arg Ser Val Gln Gly Ser Asp Gln Gly Leu
625                 630                 635                 640

Tyr His Cys Ile Ala Thr Glu Asn Ser Phe Lys Gln Thr Ile Ala Lys
                645                 650                 655

Ile Asn Phe Lys Val Leu Asp Ser Glu Met Val Ala Val Thr Asp
            660                 665                 670

Lys Trp Ser Pro Trp Thr Trp Ala Ser Val Arg Ala Leu Pro Phe
        675                 680                 685

His Pro Lys Asp Ile Met Gly Ala Phe Ser His Ser Glu Met Gln Met
    690                 695                 700

Ile Asn Gln Tyr Cys Lys Asp Thr Arg Gln Gln His Gln Gln Gly Asp
705                 710                 715                 720

Glu Ser Gln Lys Met Arg Gly Asp Tyr Gly Lys Leu Lys Ala Leu Ile
                725                 730                 735

Asn Ser Arg Lys Ser Arg Asn Arg Arg Asn Gln Leu Pro Glu Ser
            740                 745                 750

<210> SEQ ID NO 2
<211> LENGTH: 20
<212> TYPE: RNA
<213> ORGANISM: artificial sequence
<220> FEATURE:
<223> OTHER INFORMATION: interference compound for inhibiting SEMA3C
      expression

<400> SEQUENCE: 2
auggcauucc ggacaauuug                                                20

<210> SEQ ID NO 3
<211> LENGTH: 495
<212> TYPE: PRT
<213> ORGANISM: homo sapiens

<400> SEQUENCE: 3

Met Ala Phe Arg Thr Ile Cys Val Leu Val Gly Val Phe Ile Cys Ser
1               5                   10                  15

Ile Cys Val Lys Gly Ser Ser Gln Pro Gln Ala Arg Val Tyr Leu Thr
                20                  25                  30

Phe Asp Glu Leu Arg Glu Thr Lys Thr Ser Gly Tyr Phe Ser Leu Ser
            35                  40                  45

His His Pro Leu Asp Tyr Arg Ile Leu Leu Met Asp Glu Asp Gln Asp
```

```
                50                  55                  60
Arg Ile Tyr Val Gly Ser Lys Asp His Ile Leu Ser Leu Asn Ile Asn
65                  70                  75                  80

Asn Ile Ser Gln Glu Ala Leu Ser Val Phe Trp Pro Ala Ser Thr Ile
                85                  90                  95

Lys Val Glu Glu Cys Lys Met Ala Gly Lys Asp Pro Thr His Gly Cys
                100                 105                 110

Gly Asn Phe Val Arg Val Ile Gln Thr Phe Asn Arg Thr His Leu Tyr
                115                 120                 125

Val Cys Gly Ser Gly Ala Phe Ser Pro Val Cys Thr Tyr Leu Asn Arg
                130                 135                 140

Gly Arg Arg Ser Glu Asp Gln Val Phe Met Ile Asp Ser Lys Cys Glu
145                 150                 155                 160

Ser Gly Lys Gly Arg Cys Ser Phe Asn Pro Asn Val Asn Thr Val Ser
                165                 170                 175

Val Met Ile Asn Glu Glu Leu Phe Ser Gly Met Tyr Ile Asp Phe Met
                180                 185                 190

Gly Thr Asp Ala Ala Ile Phe Arg Ser Leu Thr Lys Arg Asn Ala Val
                195                 200                 205

Arg Thr Asp Gln His Asn Ser Lys Trp Leu Ser Glu Pro Met Phe Val
210                 215                 220

Asp Ala His Val Ile Pro Asp Gly Thr Asp Pro Asn Asp Ala Lys Val
225                 230                 235                 240

Tyr Phe Phe Phe Lys Glu Lys Leu Thr Asp Asn Asn Arg Ser Thr Lys
                245                 250                 255

Gln Ile His Ser Met Ile Ala Arg Ile Cys Pro Asn Asp Thr Gly Gly
                260                 265                 270

Leu Arg Ser Leu Val Asn Lys Trp Thr Thr Phe Leu Lys Ala Arg Leu
                275                 280                 285

Val Cys Ser Val Thr Asp Glu Asp Gly Pro Glu Thr His Phe Asp Glu
                290                 295                 300

Leu Glu Asp Val Phe Leu Leu Glu Thr Asp Asn Pro Arg Thr Thr Leu
305                 310                 315                 320

Val Tyr Gly Ile Phe Thr Thr Ser Ser Ser Val Phe Lys Gly Ser Ala
                325                 330                 335

Val Cys Val Tyr His Leu Ser Asp Ile Gln Thr Val Phe Asn Gly Pro
                340                 345                 350

Phe Ala His Lys Glu Gly Pro Asn His Gln Leu Ile Ser Tyr Gln Gly
                355                 360                 365

Arg Ile Pro Tyr Pro Arg Pro Gly Thr Cys Pro Gly Gly Ala Phe Thr
                370                 375                 380

Pro Asn Met Arg Thr Thr Lys Glu Phe Pro Asp Asp Val Val Thr Phe
385                 390                 395                 400

Ile Arg Asn His Pro Leu Met Tyr Asn Ser Ile Tyr Pro Ile His Lys
                405                 410                 415

Arg Pro Leu Ile Val Arg Ile Gly Thr Asp Tyr Lys Tyr Thr Lys Ile
                420                 425                 430

Ala Val Asp Arg Val Asn Ala Ala Asp Gly Arg Tyr His Val Leu Phe
                435                 440                 445

Leu Gly Thr Asp Arg Gly Thr Val Gln Lys Val Val Leu Pro Thr
                450                 455                 460

Asn Asn Ser Val Ser Gly Glu Leu Ile Leu Glu Glu Leu Glu Val Phe
465                 470                 475                 480
```

```
Lys Asn His Ala Pro Ile Thr Thr Met Lys Ile Ser Ser Lys Lys
            485                 490                 495

<210> SEQ ID NO 4
<211> LENGTH: 5189
<212> TYPE: RNA
<213> ORGANISM: homo sapiens

<400> SEQUENCE: 4
ggacugcgaa aggagcaggg uugcggagcu agggcuccag ccugcggccg cgcauucuug      60
cgucuggcca ccgcgagcu cuaaggguccg gccccgcccg guccgccccc gcggcuccu     120 gccaggcucu cgcgggcgcg cucggggugg ggccucgcgg cuggcggaga ugcggccggg    180
gcugcgcggu ggugaugcga ccugcuggg cggcgcgccg gggcagccgg agccgcgcgc    240
cgcggcgcug uaaucggaca ccaagagcgc ucgcccccgg ccuccggcca cuuuccauuc    300
acuccgaggu gccugauuga cgacgcgga gaagagcucc gggugccgcg gcacugcagc    360
gcugagauuc cuuuacaaag aaacucagag gaccggaag aaagaauuuc accuuugcga    420
cgugcuagaa auaaggucg ucugggaaaa ggacuggaga cacaagcgca uccaaccccg    480
guagcaaacu gaugacuuuu ccgucugau ucuuucaac cucgguauuu ucccuuggau     540
auuaacuugc auaucugaag aaauggcauu ccggacaauu ugcguguugg uuggaguauu    600
uauuuguucu aucugugugu aaaggaucuuc ccagccccaa gcaagagauu uuuaacauu    660 ugaugaacuu cgagaaacca agaccucuga auacuucagc cuuucccacc auccuuuaga    720
cuacaggauu uuauuaaugg augaagauca ggaccggaua uaugugggaa gcaaagauca    780
cauucuuccc cugaauauua acaauauaag ucaagaagcu ugagguguuu ucuggccagc    840
aucuacaauc aaaguugaag aaugcaaaau ggcuggcaaa gaucccacac acggcugugg    900
gaacuuuguc cguguaauuc agacuuucaa ucgcacacau uuguaugucu ugggagugg    960 cgcuuucagu ccugucugua cuuacuugaa cagaggagg agaucagagg accaaguuuu   1020
caugauugac uccaagugug aaucggaaaa aggacgcugc ucuuucaacc ccaacgugaa   1080 cacgugucu guuaugauca augaggagcu uuucucugga auguauauag auuucaucggg   1140 gacagaugcu gcuauuuuuc gaaguuuaac caagaggaau gcggucagaa cugaucaaca   1200
uaauuccaaa uggcuaagug aaccuaguguu guagaugca caugcaucc cagauggguac   1260 ugauccaaau gaugcuaagg uguacuucuu cuucaaagaa aaacugaccug acaauaacag   1320 gagcacgaaa cagauucauu ccaugauugc ucgaauaugu ccuaaugaca cugguggacu   1380
gcguagccuu gucaacaagu ggaccacuuu cuuaaaggcg aggcuggugu gcucggguaac   1440 agaugaagac ggcccagaaa cacacuuuga ugauuagag gauguuuuc ugcuggaaac    1500 ugauaacccg aggacaacac uaguguaugg cauuuuaca acaucaagcu caguuucaa    1560 aggaucagcc guguguguugu aucauuuauc ugauauacag acuguguuua augggccuuu   1620
ugcccacaaa gaaggggcca aucaucagcu gauuccuau cagggcagaa uuccauaucc    1680
ucgcccugga acuuguccag gaggagcauu uacacccaau augcgaacca ccaaggaguu    1740
cccagaugau guugucacuu uuauuccgaa ccauccucu auguacaauu ccaucuaccc    1800
aauccacaaa aggccuuga uuguugcuau uggcacugac uacaaaguaua caaagauagc    1860 uguggaucga gugaacgcug cugagggag auaccaugu cuguuucucg aacagaucg     1920 gggguacugu caaaaagugg uuguucuccc uacuaacaac ucuguccaguug gcgagcucau    1980 ucuggaggag cuggaagucu uuaagaauca ugcuccuaua acacaauga aaauuucauc    2040
```

```
uaaaaagcaa caguuguaug ugaguuccaa ugaaggggu ucccagguau cucugcaccg    2100
cugccacauc uauggua cag ccugugcuga cugcugccug gcgcgggacc cuuauugcgc   2160 cuggauggc cauccuguu ccagauucua cccaacuggg aaacggagga gccgaagaca     2220
agaugugaga cauggaaacc cacugacuca augcagagga uuuaaucuaa aagcauacag   2280
aaaugcagcu gaaauugugc aguauggagu aaaaauaaac accacuuuuc uggagugugc   2340
ccccaagucu ccgcaggcau cuaucaagug gcuguuacag aaagacaaag acaggaggaa   2400
agagguuaag cugaaugaac gaauaauagc cacuucacag ggacuccuga uccgcucugu   2460 ucagggu ucu gaccaaggac uuuaucacug cauugcuaca gaaaauaguu ucaagcagac   2520
cauagccaag aucaacuuca aaguuuuaga uucagaaaug guggcuguug ugacggacaa   2580 augguccccca uggaccuggg ccagcucugu gagggcuuua cccuuccacc cgaaggacau   2640
caugggggca uucagccacu cagaaaugca gaugauuaac caauauugca aagacacucg   2700
gcagcaacau cagcagggag augaaucaca gaaaaugaga ggggacuaug gcaaguuaaa   2760
ggcccucauc aauagucgga aaaguagaaa caggaggaau caguugccag agucauaaua   2820
uuuucuuaug ugggucuuau gcuuccauua acaaaugcuc ugcuucaau gaucaaauuu    2880 ugagcaaaga aacuugugcu uuaccaaggg gaauuacuga aaaaggugau uacuccugaa   2940
gugaguuuua cacgaacuga aaugagcaug cauuuucuug uaugauagug acuagcacua   3000
gacaugucau gguccucaug gugcauauaa auauauuuaa cuuaacccag auuuuauuua   3060
uaucuuuauu caccuuuucu ucaaaaucga uaugguggcu gcaaaacuag aauuguugca   3120
ucccucaauu gaaugagggc cauaucccug ugguauuccu uccugcuuu ggggcuuuag    3180 aauucuaauu gucaguugauu uuguauauga aaacaaguuc caaauccaca gcuuuuacgu   3240
aguaaaaguc auaaaugcau augacagaau ggcuaucaaa agaaauagaa aaggaagacg   3300
gcauuuaaag uuguauaaaa acacgaguua ucauaaaga gaaaaugaug aguuuuuaug   3360
guuccaauga aauauguugg gguuuuuuua agauguaaa aauaaucagu acugguuauc    3420
ugucacugac cuuuguuucc uuauucagga agauaaaaau caguaaccua ccccaugaag   3480 auauuugguug ggaguuauau cagugaagca guuuggguua uauucuuaug uuaucaccuu   3540
ccaaacaaaa gcacuacuu uuuuuggaag uuauuuauuu uagacucaaa gaauauaauc    3600
uugcacuacu caguuauuac uguuuguucu cuuauucccu agucugugug gcaaauuaaa   3660
caauauaaga aggaaaaauu ugaaguauua gacucuaaaa uaaggggauga aucaucaga   3720 aagaaaaauc aaagu agaaa cuacuaauuu uuuaagagga auuuauaaca aauauggcuu   3780
guuuucaacu ucaguacuca aauucaauga ucuucccuuu uauuaaaacc agucucagau   3840 aucuacuga uuuuuaaguc aacacuauau auuuuaugau cuuuucagug ugauggcaag    3900 gugcuugua ugucuagaaa guaagaaaac aauaugagga gacauucugu cuuucaaaag    3960 guaauggac uauacguucac ugucucuaa gguaaaagu aguaaauuu ugaugaauaa      4020 aaauaauuau cuccuaauug uauguuagaa uaauuuauu agaauaauuu cauacugaaa     4080
uuauuuucuc caaauaaaaa uuagauggaa aaugugaaaa aaaauuauuc augcucucau    4140 auauauuua aaaacacuac uuuugcuuuu uuauuuaccu uuuaagacau uucaugcuu      4200 ccagguaaaa acagauauug uaccauguac cuaauccaaa uaucauauaa acauuuuauu    4260
uauaguuaau aaucuaugau gaagguaauu aaguagauu auggccuuuu uaaguauugc    4320
agucuaaaac uucaaaaacu aaaaucauug ucaaaauuaa uaugauuauu aaucagaaua    4380
```

```
ucagaauaug auucacuauu uaaacuauga uaaauuauga uaauauauga ggaggccucg   4440
cuauagcaaa aauaguuaaa augcugacau aacaccaaac uucauuuuuu aaaaaaucug   4500 uuguccaaa uguguauaau uuuaaaguaa uuucuaaagc aguuuauuau aaugguuugc    4560
cugcuuaaaa gguauaauua aacuucuuuu cucuucuaca uugacacaca gaaaugaguc   4620
aauguaaagc caaaccauc uucuguguuu auggccaauc uauucucaaa guuaaaagua    4680
aaauuguuuc agagucacag uucccuuuau uucacauaag cccaaacuga uagacaguaa   4740
cggguguuag uuuuauacua uauuugugcu auuuaauucu uucuauuuuc acaauuauua   4800
aauuguguac acuuucauua cuuuuaaaaa uguagaaauu cuucaugaac auaacucugc   4860
ugaauguaaa agaaaauuuu uuucaaaaa ugcuguuaau guauacuacu ggugguugau    4920
ugguuuuauu uuauguagcu ugacaauuca gugacuuaau aucauucca uuuguauugu    4980 acauaaaauu uucuagaaau acacuuuuuu ccaaagugua aguuugugaa uagauuuuag   5040
caugaugaaa cugucauaau ggugaauguu caaucugugu aagaaaacaa acuaaauga    5100 guugucacac uaaauuuaa uuggauauug augaaaucau uggccuggca aauaaaaca     5160 uguugaauuc cccaaaaaaa aaaaaaaaa                                    5189
```

<210> SEQ ID NO 5
<211> LENGTH: 20
<212> TYPE: DNA
<213> ORGANISM: artificial sequence
<220> FEATURE:
<223> OTHER INFORMATION: interference compound for inhibiting SEMA3C
       expression

<400> SEQUENCE: 5
aatattatga ctctggcaac                                               20

<210> SEQ ID NO 6
<211> LENGTH: 20
<212> TYPE: DNA
<213> ORGANISM: artificial sequence
<220> FEATURE:
<223> OTHER INFORMATION: interference compound for inhibiting SEMA3C
       expression

<400> SEQUENCE: 6
tgattcctcc tgtttctact                                               20

<210> SEQ ID NO 7
<211> LENGTH: 20
<212> TYPE: DNA
<213> ORGANISM: artificial sequence
<220> FEATURE:
<223> OTHER INFORMATION: interference compound for inhibiting SEMA3C
       expression

<400> SEQUENCE: 7
tttccgacta ttgatgaggg                                               20

<210> SEQ ID NO 8
<211> LENGTH: 20
<212> TYPE: DNA
<213> ORGANISM: artificial sequence
<220> FEATURE:
<223> OTHER INFORMATION: interference compound for inhibiting SEMA3C
       expression

<400> SEQUENCE: 8
cctttaactt gccatagtcc                                               20

```
<210> SEQ ID NO 9
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 9
cctctcattt tctgtgattc                                              20

<210> SEQ ID NO 10
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 10
atctccctgc tgatgttgct                                              20

<210> SEQ ID NO 11
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 11
gccgagtgtc tttgcaatat                                              20

<210> SEQ ID NO 12
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 12
tggttaatca tctgcatttc                                              20

<210> SEQ ID NO 13
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 13
tgagtggctg aatgccccca                                              20

<210> SEQ ID NO 14
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 14
tgatgtcctt cgggtggaag                                              20
```

```
<210> SEQ ID NO 15
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 15
ggtaaagccc tcacagagct                                           20

<210> SEQ ID NO 16
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 16
ggcccaggtc catggggacc                                           20

<210> SEQ ID NO 17
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 17
atttgtccgt cacaacagcc                                           20

<210> SEQ ID NO 18
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 18
accatttctg aatctaaaac                                           20

<210> SEQ ID NO 19
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 19
tttgaagttg atcttggcta                                           20

<210> SEQ ID NO 20
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 20
tggtctgctt gaaactattt                                           20
```

```
<210> SEQ ID NO 21
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 21
tctgtagcaa tgcagtgata                                              20

<210> SEQ ID NO 22
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 22
aagtccttgg tcagaaccct                                              20

<210> SEQ ID NO 23
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 23
gaacagagcg gatcaggagt                                              20

<210> SEQ ID NO 24
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 24
ccctgtgaag tggctattat                                              20

<210> SEQ ID NO 25
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 25
tcgttcattc agcttaacct                                              20

<210> SEQ ID NO 26
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 26
ctttcctcct gtctttgtct                                              20

<210> SEQ ID NO 27
```

-continued

<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 27
ttctgtaaca gccacttgat                                               20

<210> SEQ ID NO 28
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 28
agatgcctgc ggagacttgg                                               20

<210> SEQ ID NO 29
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 29
gggcacactc cagaaaagtg                                               20

<210> SEQ ID NO 30
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 30
gtgttatttt ttactccata                                               20

<210> SEQ ID NO 31
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 31
ctgcacaatt tcagctgcat                                               20

<210> SEQ ID NO 32
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 32
ttctgtatgc ttttagatta                                               20

<210> SEQ ID NO 33
<211> LENGTH: 20

```
<212> TYPE: DNA
<213> ORGANISM: artificial sequence
<220> FEATURE:
<223> OTHER INFORMATION: interference compound for inhibiting SEMA3C
      expression

<400> SEQUENCE: 33
aatcctctgc attgagtcag                                                   20

<210> SEQ ID NO 34
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 34
tgggtttcca tgtctcacat                                                   20

<210> SEQ ID NO 35
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 35
cttgtcttcg gctcctccgt                                                   20

<210> SEQ ID NO 36
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 36
ttcccagttg ggtagaatct                                                   20

<210> SEQ ID NO 37
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 37
ggaacaggaa tggccatccc                                                   20

<210> SEQ ID NO 38
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 38
aggcgcaata agggtcccgc                                                   20

<210> SEQ ID NO 39
<211> LENGTH: 20
<212> TYPE: DNA
```

```
<213> ORGANISM: artificial sequence
<220> FEATURE:
<223> OTHER INFORMATION: interference compound for inhibiting SEMA3C
      expression

<400> SEQUENCE: 39
gccaggcagc agtcagcaca                                              20

<210> SEQ ID NO 40
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 40
ggctgtacca tagatgtggc                                              20

<210> SEQ ID NO 41
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 41
agcggtgcag agatacctgg                                              20

<210> SEQ ID NO 42
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 42
gaaacccctt cattggaact                                              20

<210> SEQ ID NO 43
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 43
cacatacaac tgttgctttt                                              20

<210> SEQ ID NO 44
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 44
tagatgaaat tttcattgtt                                              20

<210> SEQ ID NO 45
<211> LENGTH: 20
<212> TYPE: DNA
<213> ORGANISM: artificial sequence
```

```
<220> FEATURE:
<223> OTHER INFORMATION: interference compound for inhibiting SEMA3C
      expression

<400> SEQUENCE: 45
gttataggag catgattctt                                                    20

<210> SEQ ID NO 46
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 46
aaagacttcc agctcctcca                                                    20

<210> SEQ ID NO 47
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 47
gaatgagctc gccactgaca                                                    20

<210> SEQ ID NO 48
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 48
gagttgttag taggaagaac                                                    20

<210> SEQ ID NO 49
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 49
aaccactttt tgcacagtac                                                    20

<210> SEQ ID NO 50
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 50
cccgatctgt tccgagaaac                                                    20

<210> SEQ ID NO 51
<211> LENGTH: 20
<212> TYPE: DNA
<213> ORGANISM: artificial sequence
<220> FEATURE:
```

```
<223> OTHER INFORMATION: interference compound for inhibiting SEMA3C
      expression

<400> SEQUENCE: 51
aggacatggt atctcccatc                                                      20

<210> SEQ ID NO 52
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 52
agcagcgttc actcgatcca                                                      20

<210> SEQ ID NO 53
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 53
cagctatctt tgtatacttg                                                      20

<210> SEQ ID NO 54
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 54
tagtcagtgc caatacgaac                                                      20

<210> SEQ ID NO 55
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 55
aatcaaaggc cttttgtgga                                                      20

<210> SEQ ID NO 56
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 56
ttgggtagat ggaattgtac                                                      20

<210> SEQ ID NO 57
<211> LENGTH: 20
<212> TYPE: DNA
<213> ORGANISM: artificial sequence
<220> FEATURE:
<223> OTHER INFORMATION: interference compound for inhibiting SEMA3C
``` expression

<400> SEQUENCE: 57
atgagaggat ggttccgaat                                                  20

<210> SEQ ID NO 58
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 58
aaaagtgaca acatcatctg                                                  20

<210> SEQ ID NO 59
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 59
ggaactcctt ggtggttcgc                                                  20

<210> SEQ ID NO 60
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 60
atattgggtg taaatgctcc                                                  20

<210> SEQ ID NO 61
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 61
tcctggacaa gttccagggc                                                  20

<210> SEQ ID NO 62
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 62
gaggatatgg aattctgccc                                                  20

<210> SEQ ID NO 63
<211> LENGTH: 20
<212> TYPE: DNA
<213> ORGANISM: artificial sequence
<220> FEATURE:
<223> OTHER INFORMATION: interference compound for inhibiting SEMA3C
      expression -continued

<400> SEQUENCE: 63
tgataggaaa tcagctgatg                                           20

<210> SEQ ID NO 64
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 64
attgggccct tctttgtggg                                           20

<210> SEQ ID NO 65
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 65
caaaaggccc attaaacaca                                           20

<210> SEQ ID NO 66
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 66
gtctgtatat cagataaatg                                           20

<210> SEQ ID NO 67
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 67
atacacacac acggctgatc                                           20

<210> SEQ ID NO 68
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 68
ctttgaaaac tgagcttgat                                           20

<210> SEQ ID NO 69
<211> LENGTH: 20
<212> TYPE: DNA
<213> ORGANISM: artificial sequence
<220> FEATURE:
<223> OTHER INFORMATION: interference compound for inhibiting SEMA3C
      expression

```
<400> SEQUENCE: 69
gttgtaaaaa tgccatacac                                               20

<210> SEQ ID NO 70
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 70
tagtgttgtc ctcgggttat                                               20

<210> SEQ ID NO 71
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 71
cagtttccag cagaaacaca                                               20

<210> SEQ ID NO 72
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 72
tcctctaatt catcaaagtg                                               20

<210> SEQ ID NO 73
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 73
tgtttctggg ccgtcttcat                                               20

<210> SEQ ID NO 74
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 74
ctgttaccga gcacaccagc                                               20

<210> SEQ ID NO 75
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 75
```

```
ctcgccttta agaaagtggt                                              20
```

<210> SEQ ID NO 76
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 76

```
ccacttgttg acaaggctac                                              20
```

<210> SEQ ID NO 77
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 77

```
gcagtccacc agtgtcatta                                              20
```

<210> SEQ ID NO 78
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 78

```
ggacatattc gagcaatcat                                              20
```

<210> SEQ ID NO 79
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 79

```
ggaatgaatc tgtttcgtgc                                              20
```

<210> SEQ ID NO 80
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 80

```
tcctgttatt gtcagtcagt                                              20
```

<210> SEQ ID NO 81
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 81

```
ttttctttga agaagaagta                                          20

<210> SEQ ID NO 82
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 82
caccttagca tcatttggat                                          20

<210> SEQ ID NO 83
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 83
cagtaccatc tgggatgaca                                          20

<210> SEQ ID NO 84
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 84
tgtgcatcta caaacatagg                                          20

<210> SEQ ID NO 85
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 85
ttcacttagc catttggaat                                          20

<210> SEQ ID NO 86
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 86
tatgttgatc agttctgacc                                          20

<210> SEQ ID NO 87
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 87
gcattcctct tggttaaact                                          20
```

```
<210> SEQ ID NO 88
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 88
tcgaaaaata gcagcatctg                                              20

<210> SEQ ID NO 89
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 89
tccccatgaa atctatatac                                              20

<210> SEQ ID NO 90
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 90
attccagaga aaagctcctc                                              20

<210> SEQ ID NO 91
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 91
attgatcata acagacaccg                                              20

<210> SEQ ID NO 92
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 92
tgttcacgtt ggggttgaaa                                              20

<210> SEQ ID NO 93
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 93
gagcagcgtc cttttccaga                                              20
```

<210> SEQ ID NO 94
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 94
ttcacacttg gagtcaatca                                              20

<210> SEQ ID NO 95
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 95
tgaaaacttg gtcctctgat                                              20

<210> SEQ ID NO 96
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 96
ctcctccctc tgttcaagta                                              20

<210> SEQ ID NO 97
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 97
agtacagaca ggactgaaag                                              20

<210> SEQ ID NO 98
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 98
cgccactccc acagacatac                                              20

<210> SEQ ID NO 99
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 99
aaatgtgtgc gattgaaagt                                              20

```
<210> SEQ ID NO 100
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 100
ctgaattaca cggacaaagt                                              20

<210> SEQ ID NO 101
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 101
tcccacagcc gtgtgtggga                                              20

<210> SEQ ID NO 102
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 102
tctttgccag ccattttgca                                              20

<210> SEQ ID NO 103
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 103
ttcttcaact ttgattgtag                                              20

<210> SEQ ID NO 104
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 104
atgctggcca gaaaacactc                                              20

<210> SEQ ID NO 105
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 105
aaagcttctt gacttatatt                                              20

<210> SEQ ID NO 106
```

```
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 106
gttaatattc agggaaagaa                                              20

<210> SEQ ID NO 107
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 107
tgtgatcttt gcttcccaca                                              20

<210> SEQ ID NO 108
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 108
tatatccggt cctgatcttc                                              20

<210> SEQ ID NO 109
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 109
atccattaat aaaatcctgt                                              20

<210> SEQ ID NO 110
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 110
agtctaaagg atggtgggaa                                              20

<210> SEQ ID NO 111
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 111
aggctgaagt attcagaggt                                              20

<210> SEQ ID NO 112
<211> LENGTH: 20
```

```
<212> TYPE: DNA
<213> ORGANISM: artificial sequence
<220> FEATURE:
<223> OTHER INFORMATION: interference compound for inhibiting SEMA3C
      expression

<400> SEQUENCE: 112
cttggtttct cgaagttcat                                              20

<210> SEQ ID NO 113
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 113
caaatgttaa ataaactctt                                              20

<210> SEQ ID NO 114
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 114
gcttggggct gggaagatcc                                              20

<210> SEQ ID NO 115
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 115
tttcacacag atagaacaaa                                              20

<210> SEQ ID NO 116
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 116
taaatactcc aaccaacacg                                              20

<210> SEQ ID NO 117
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 117
caaattgtcc ggaatgccat                                              20

<210> SEQ ID NO 118
<211> LENGTH: 20
<212> TYPE: DNA
```

```
<213> ORGANISM: artificial sequence
<220> FEATURE:
<223> OTHER INFORMATION: interference compound for inhibiting SEMA3C
      expression

<400> SEQUENCE: 118
ctttgccagc cattttgcat                                                       20

<210> SEQ ID NO 119
<211> LENGTH: 20
<212> TYPE: DNA
<213> ORGANISM: artificial sequence
<220> FEATURE:
<223> OTHER INFORMATION: interference compound for inhibiting SEMA3C
      expression

<400> SEQUENCE: 119
tacctgggaa acccttcat                                                        20
```

SEMAPHORIN 3C (SEMA3C) INHIBITOR THERAPEUTICS, METHODS, AND USES

RELATED APPLICATIONS

This application claims priority to U.S. provisional patent application 61/202,756 filed 1 Apr. 2009.

FIELD OF THE INVENTION

The present invention relates to compositions and methods for the treatment of cancer. The invention more specifically relates to potential therapeutics for treatment of prostate cancer.

BACKGROUND

Among American men, advanced prostate cancer (CaP) is presently the most frequently diagnosed cancer and is the second leading causes of cancer-related deaths. In 2009, an estimated 192,280 American men will be diagnosed with CaP and 27,360 will die of the disease. While early stage disease is frequently curable with surgery or radiation therapy, approximately ⅓ of patients clinically present with locally advanced or metastatic disease that is associated with a poor prognosis. Therapeutic androgen suppression through surgical or medical castration still remains the most effective therapy for advanced CaP since its inception in 1941 by Charles Huggins (Huggins and Hodges 1941). Androgen suppression consistently induces tumour regression in over 80% of patients with advanced disease due to the exquisite dependence of CaP cells on the androgen signaling axis for their growth and survival (Isaacs et al. 1997). Furthermore, Androgen Receptor (AR) expression is maintained throughout prostate cancer progression, and the majority of androgen independent or hormone refractory prostate cancers express AR (Heinlein and Chang 2004). However, despite initial success in achieving significant and tangible clinical responses, the duration of progression-free survival remains transient (~1-3 years) and progression to lethal castration-resistant disease (also frequently referred to as androgen independent or hormone refractory disease) is essentially universal (Bruchovsky et al. 1988; Goldenberg et al. 1988; Bruchovsky et al. 1989). Thus, the current standard of care for patients with Castration-Resistant Prostate Cancer (CRPC) remains only palliative, with chemotherapy—eg. docetaxel (Petrylak et al. 2004; Tannock et al. 2004) inducing only marginal survival benefits at a cost of, at times, significant morbidity.

Semaphorins are a large family of highly conserved secreted or cell surface signaling proteins that were originally identified as mediators of cell migration and axon guidance in the developing nervous system (Tamagnone and Comoglio 2000; Kruger et al. 2005). While semaphorins have been best characterized in the nervous system, they are known to be expressed in other tissues. Semaphorins have been implicated in a variety of dynamic physiological processes including angiogenesis, tissue morphogenesis, and immunity (Kolodkin et al. 1993; Kruger et al. 2005). Semaphorins regulate numerous biological responses including cell proliferation, adhesion, migration and apoptosis through interaction of semaphorins with their cognate receptors, plexins. Plexins are single pass transmembrane receptors that have highly conserved intracellular domains that have intrinsic GAP (GTPase-activating protein) activity towards R-Ras12 (Negishi et al. 2005). Nine vertebrate plexins have been identified, grouped into four subfamilies (Plexin A to D) based on computational phylogenetic analyses. Semaphorins and plexins both express a conserved 500 amino acid extracellular motif called the SEMA domain that is thought to be involved in protein-protein interactions. Membrane-associated semaphorins bind directly to plexins whereas secreted semaphorins, often have an additional binding component (either neuropilins 1 or 2 (Npn-1 or Npn-2)) as co-receptors. Plexins are thought to regulate the actin cytoskeleton by controlling the activity of the small GTPases, Rnd1, R-Ras, Rac and Rho12. When plexins bind to semaphorin they are thought to also interact with and activate the receptor tyrosine kinases, Her2/neu (ErbB2), and hepatocyte growth factor/scatter factor receptor (c-Met) (Giordano et al. 2002; Swiercz et al. 2004; Swiercz et al. 2008).

SEMA3C is a member of the class 3 semaphorins, which are a subfamily of secreted semaphorins (Tamagnone and Comoglio 2000; Verras et al. 2007). SEMA3C may mediate opposing effects depending on the target cell type. For example, SEMA3C provides chemorepulsive axon guidance to sympathetic neurons whereas SEMA3C provides chemoattractive guidance for GABAnergic neurons. The specificity of semaphorin signals in each cell type depends on the combination of neuropilin/plexin present and their association with accessory receptors. SEMA3C has been shown to bind to receptor complexes comprised of Plexin A1, A2, or B1 in association with either Npn-1 or Npn-210. Plexins can actively influence their binding affinity (and possibly selectivity) for the different subsets of secreted semaphorins. For example, the binding of SEMA3C to neuropilins seems to be inhibited by the co-expression of plexin A1, whereas it is increased in the presence of plexin A2 or B1.

Herman and Meadows (2007) suggest an association between SEMA3C expression and increased invasion and adhesion in PC-3 AR negative cancer cells. However, AR negative prostate cancers represent a small minority of late stage androgen independent prostate cancers (Heinlein and Chang 2004).

SUMMARY OF THE INVENTION

The present invention is based, in part, on the surprising discovery that SEMA3C plays a significant role in the progression of androgen receptor (AR) positive prostate cancer and in androgen dependent prostate cancer.

In accordance with a first embodiment, there is provided a method for treating prostate cancer comprising administering a biologically effective amount of a SEMA3C inhibitor to prostate cancer cells. The biologically effective amount may be an amount sufficient to cause cell death of a prostate cancer cell or to inhibit proliferation of the prostate cancer cells.

In accordance with another embodiment, there is provided a method for killing or inhibiting the proliferation of androgen receptor (AR) positive prostate cancer including contacting the prostate cancer with a biologically effective amount of a composition comprising at least one SEMA3C inhibitor.

In accordance with another embodiment, there is provided a method of inhibiting growth of an androgen dependent prostate cancer including administering androgen deprivation therapy and a SEMA3C inhibitor. The androgen deprivation therapy and the SEMA3C inhibitor may be initiated at about the same time. The SEMA3C inhibitor may be initiated after androgen deprivation therapy and before the androgen dependent cancer becomes androgen independent.

In accordance with another embodiment, there is provided a use of a SEMA3C inhibitor for the preparation of a medicament to treat prostate cancer.

In accordance with another embodiment, there is provided a use of a SEMA3C inhibitor to treat prostate cancer.

In accordance with another embodiment, there is provided a SEMA3C inhibitor for the treatment of prostate cancer.

In accordance with another embodiment, there is provided a pharmaceutical composition including a SEMA3C inhibitor in combination with a physiologically acceptable carrier.

In accordance with another embodiment, there is provided a commercial package including a SEMA3C inhibitor and optionally including instructions for use in the treatment of prostate cancer.

In accordance with another embodiment, there is provided isolated nucleic acids and amino acids as described herein. For example, SEQ ID NOs: 2 and 5-119.

In a further aspect, the invention relates to methods for treating a patient afflicted with prostate cancer or at risk of developing prostate cancer. Such methods may comprise reducing the expression and/or interfering with the biological function of SEMA3C. In an embodiment, the method comprises providing to the patient an antisense oligonucleotide or polynucleotide complementary to SEMA3C, or a segment thereof. For example, an antisense polynucleotide may be provided to the patient through the delivery of a vector that expresses an anti-sense polynucleotide of SEMA3C or a fragment thereof. In another embodiment, the method comprises providing to the patient an antibody, an antibody derivative, or antibody fragment, which binds specifically with the SEMA3C protein or a fragment of the protein. In another embodiment, the antibody, antibody derivative or antibody fragment binds specifically with a protein having the sequence of a SEQ ID NO:3, or a fragment of SEMA3C.

The prostate cancer may be an androgen receptor (AR) positive prostate cancer. The prostate cancer may be an androgen dependent prostate cancer. The prostate cancer may be a prostate adenocarcinoma. The prostate cancer may be an AR positive prostate adenocarcinoma. The prostate cancer may be an androgen dependent prostate adenocarcinoma. Alternatively, the cancer may be another type of cancer as described herein. The cancer may be an AR positive cancer. The cancer may be an androgen dependent cancer.

The SEMA3C inhibitor may be selected from one or more of the following: an antibody, a SEMA3C peptide, an antisense RNA, an interfering RNA (RNAi) (for example, but not limited to: a siRNA; a sisiRNA; a tsiRNA; a RNA-DNA chimeric duplex; a tkRNA; a Dicer-substrate dsRNA; a shRNA; a tRNA-shRNA; a aiRNA; a pre-miRNA; a pri-miRNA mimic; a pri-miRNA mimic cluster; a transcriptional gene silencing (TGS); and combinations thereof), a small molecule, or combinations thereof. The antibody may be selected from one or more of the following: a polyclonal antibody; a monoclonal antibody; or a fragment thereof; a single chain Fc region (scFc); or an intrabody. The antisense RNA may include about 15 to 50 nucleotides that are at least 80% identical to any 15 to 50 contiguous nucleotides selected from SEQ ID NO:4. The antisense RNA may include about 17 to 30 nucleotides that are at least 80% identical to any 17 to 30 contiguous nucleotides selected from SEQ ID NO:4. The antisense RNA may include about 19 to 25 nucleotides that are at least 80% identical to any 19 to 25 contiguous nucleotides selected from SEQ ID NO:4. The antisense RNA may include the nucleotides of SEQ ID NO:2. Alternatively, the antisense RNA may include one or more of the nucleotides set out in TABLE 2 (SEQ ID NOs:5-119) or a sequence at least 80% identical thereto. The RNAi that inhibits SEMA3C may include a double stranded region, having a sense and an antisense strand, of about 15 to 50 nucleotides, and wherein the sense strand may be at least 80% identical to any 15 to 50 contiguous nucleotides selected from SEQ ID NO:4. The RNAi that inhibits SEMA3C may include a double stranded region, having a sense and an antisense strand, of about 17 to 30 nucleotides, and wherein the sense strand may be at least 80% identical to any 17 to 30 contiguous nucleotides selected from SEQ ID NO:4. The RNAi that inhibits SEMA3C may include a double stranded region, having a sense and an antisense strand, of about 19 to 25 nucleotides, and wherein the sense strand may be at least 80% identical to any 19 to 25 contiguous nucleotides selected from SEQ ID NO:4. The RNAi that inhibits SEMA3C may include a double stranded region, having a sense and an antisense strand, and wherein the sense strand may be SEQ ID NO:2. Alternatively, the RNAi that inhibits SEMA3C may include a double stranded region, having a sense and an antisense strand, and wherein the sense strand may be selected from TABLE 2 (SEQ ID NOs:5-119) or a sequence at least 80% identical thereto. The small molecule may be 2-bromo-N-(2-methoxyphenyl)propanamide.

The SEMA3C peptide may include at least 20 contiguous amino acids of the SEMA domain set out in SEQ ID NO:3. The SEMA3C peptide may include at least 25 contiguous amino acids of the SEMA domain set out in SEQ ID NO:3. The SEMA3C peptide may include at least 30 contiguous amino acids of the SEMA domain set out in SEQ ID NO:3. The SEMA3C peptide may include at least 35 contiguous amino acids of the SEMA domain set out in SEQ ID NO:3. The SEMA3C peptide may include at least 40 contiguous amino acids of the SEMA domain set out in SEQ ID NO:3. The SEMA3C peptide may include at least 45 contiguous amino acids of the SEMA domain set out in SEQ ID NO:3. The SEMA3C peptide may include at least 50 contiguous amino acids of the SEMA domain set out in SEQ ID NO:3. The SEMA3C peptide may include at least 55 contiguous amino acids of the SEMA domain set out in SEQ ID NO:3. The SEMA3C peptide may include at least 60 contiguous amino acids of the SEMA domain set out in SEQ ID NO:3. The SEMA3C peptide may include at least 65 contiguous amino acids of the SEMA domain set out in SEQ ID NO:3. The SEMA3C peptide may include at least 70 contiguous amino acids of the SEMA domain set out in SEQ ID NO:3. The SEMA3C peptide may include at least 75 contiguous amino acids of the SEMA domain set out in SEQ ID NO:3. The SEMA3C peptide may include at least 80 contiguous amino acids of the SEMA domain set out in SEQ ID NO:3. The SEMA3C peptide may include at least 85 contiguous amino acids of the SEMA domain set out in SEQ ID NO:3. The SEMA3C peptide may include at least 90 contiguous amino acids of the SEMA domain set out in SEQ ID NO:3. The SEMA3C peptide may include at least 95 contiguous amino acids of the SEMA domain set out in SEQ ID NO:3. The SEMA3C peptide may include at least 100 contiguous amino acids of the SEMA domain set out in SEQ ID NO:3. The SEMA3C peptide may include at least 105 contiguous amino acids of the SEMA domain set out in SEQ ID NO:3. The SEMA3C peptide may include at least 110 contiguous amino acids of the SEMA domain set out in SEQ ID NO:3. The SEMA3C peptide may include at least 115 contiguous amino acids of the SEMA domain set out in SEQ ID NO:3. The SEMA3C peptide may include at least 120 contiguous amino acids of the SEMA domain set out in SEQ ID NO:3. The SEMA3C peptide may include at least 125 contiguous amino acids of the SEMA domain set out in SEQ ID NO:3. The SEMA3C peptide may include at least 130 contiguous amino acids of the SEMA domain set out in SEQ ID NO:3. The SEMA3C peptide may include at least 135 contiguous amino acids of the SEMA domain set out in SEQ ID NO:3. The SEMA3C peptide may include at least 140 contiguous amino acids of the SEMA domain set out in SEQ ID NO:3.

The SEMA3C peptide may include at least 145 contiguous amino acids of the SEMA domain set out in SEQ ID NO:3. The SEMA3C peptide may include at least 150 contiguous amino acids of the SEMA domain set out in SEQ ID NO:3. The SEMA3C peptide may include at least 155 contiguous amino acids of the SEMA domain set out in SEQ ID NO:3. The SEMA3C peptide may include at least 160 contiguous amino acids of the SEMA domain set out in SEQ ID NO:3. The SEMA3C peptide may include at least 165 contiguous amino acids of the SEMA domain set out in SEQ ID NO:3. The SEMA3C peptide may include at least 170 contiguous amino acids of the SEMA domain set out in SEQ ID NO:3. The SEMA3C peptide may include at least 175 contiguous amino acids of the SEMA domain set out in SEQ ID NO:3. The SEMA3C peptide may include at least 180 contiguous amino acids of the SEMA domain set out in SEQ ID NO:3. The SEMA3C peptide may include at least 185 contiguous amino acids of the SEMA domain set out in SEQ ID NO:3. The SEMA3C peptide may include at least 190 contiguous amino acids of the SEMA domain set out in SEQ ID NO:3. The SEMA3C peptide may include at least 195 contiguous amino acids of the SEMA domain set out in SEQ ID NO:3. The SEMA3C peptide may include at least 200 contiguous amino acids of the SEMA domain set out in SEQ ID NO:3. The SEMA3C peptide may include at least 205 contiguous amino acids of the SEMA domain set out in SEQ ID NO:3. The SEMA3C peptide may include at least 210 contiguous amino acids of the SEMA domain set out in SEQ ID NO:3. The SEMA3C peptide may include at least 215 contiguous amino acids of the SEMA domain set out in SEQ ID NO:3. The SEMA3C peptide may include at least 220 contiguous amino acids of the SEMA domain set out in SEQ ID NO:3. The SEMA3C peptide may include at least 225 contiguous amino acids of the SEMA domain set out in SEQ ID NO:3. The SEMA3C peptide may include at least 230 contiguous amino acids of the SEMA domain set out in SEQ ID NO:3. The SEMA3C peptide may include at least 235 contiguous amino acids of the SEMA domain set out in SEQ ID NO:3. The SEMA3C peptide may include at least 240 contiguous amino acids of the SEMA domain set out in SEQ ID NO:3. The SEMA3C peptide may include at least 245 contiguous amino acids of the SEMA domain set out in SEQ ID NO:3. The SEMA3C peptide may include at least 250 contiguous amino acids of the SEMA domain set out in SEQ ID NO:3. The SEMA3C peptide may include at least 255 contiguous amino acids of the SEMA domain set out in SEQ ID NO:3. The SEMA3C peptide may include at least 260 contiguous amino acids of the SEMA domain set out in SEQ ID NO:3. The SEMA3C peptide may include at least 265 contiguous amino acids of the SEMA domain set out in SEQ ID NO:3. The SEMA3C peptide may include at least 270 contiguous amino acids of the SEMA domain set out in SEQ ID NO:3. The SEMA3C peptide may include at least 275 contiguous amino acids of the SEMA domain set out in SEQ ID NO:3. The SEMA3C peptide may include at least 280 contiguous amino acids of the SEMA domain set out in SEQ ID NO:3. The SEMA3C peptide may include at least 285 contiguous amino acids of the SEMA domain set out in SEQ ID NO:3. The SEMA3C peptide may include at least 290 contiguous amino acids of the SEMA domain set out in SEQ ID NO:3. The SEMA3C peptide may include at least 295 contiguous amino acids of the SEMA domain set out in SEQ ID NO:3. The SEMA3C peptide may include at least 300 contiguous amino acids of the SEMA domain set out in SEQ ID NO:3. The SEMA3C peptide may include at least 305 contiguous amino acids of the SEMA domain set out in SEQ ID NO:3. The SEMA3C peptide may include at least 310 contiguous amino acids of the SEMA domain set out in SEQ ID NO:3. The SEMA3C peptide may include at least 315 contiguous amino acids of the SEMA domain set out in SEQ ID NO:3. The SEMA3C peptide may include at least 320 contiguous amino acids of the SEMA domain set out in SEQ ID NO:3. The SEMA3C peptide may include at least 325 contiguous amino acids of the SEMA domain set out in SEQ ID NO:3. The SEMA3C peptide may include at least 330 contiguous amino acids of the SEMA domain set out in SEQ ID NO:3. The SEMA3C peptide may include at least 335 contiguous amino acids of the SEMA domain set out in SEQ ID NO:3. The SEMA3C peptide may include at least 340 contiguous amino acids of the SEMA domain set out in SEQ ID NO:3. The SEMA3C peptide may include at least 345 contiguous amino acids of the SEMA domain set out in SEQ ID NO:3. The SEMA3C peptide may include at least 350 contiguous amino acids of the SEMA domain set out in SEQ ID NO:3. The SEMA3C peptide may include at least 355 contiguous amino acids of the SEMA domain set out in SEQ ID NO:3. The SEMA3C peptide may include at least 360 contiguous amino acids of the SEMA domain set out in SEQ ID NO:3. The SEMA3C peptide may include at least 365 contiguous amino acids of the SEMA domain set out in SEQ ID NO:3. The SEMA3C peptide may include at least 370 contiguous amino acids of the SEMA domain set out in SEQ ID NO:3. The SEMA3C peptide may include at least 375 contiguous amino acids of the SEMA domain set out in SEQ ID NO:3. The SEMA3C peptide may include at least 380 contiguous amino acids of the SEMA domain set out in SEQ ID NO:3. The SEMA3C peptide may include at least 385 contiguous amino acids of the SEMA domain set out in SEQ ID NO:3. The SEMA3C peptide may include at least 390 contiguous amino acids of the SEMA domain set out in SEQ ID NO:3. The SEMA3C peptide may include at least 395 contiguous amino acids of the SEMA domain set out in SEQ ID NO:3. The SEMA3C peptide may include at least 400 contiguous amino acids of the SEMA domain set out in SEQ ID NO:3. The SEMA3C peptide may include at least 405 contiguous amino acids of the SEMA domain set out in SEQ ID NO:3. The SEMA3C peptide may include at least 410 contiguous amino acids of the SEMA domain set out in SEQ ID NO:3. The SEMA3C peptide may include at least 415 contiguous amino acids of the SEMA domain set out in SEQ ID NO:3. The SEMA3C peptide may include at least 420 contiguous amino acids of the SEMA domain set out in SEQ ID NO:3. The SEMA3C peptide may include at least 425 contiguous amino acids of the SEMA domain set out in SEQ ID NO:3. The SEMA3C peptide may include at least 430 contiguous amino acids of the SEMA domain set out in SEQ ID NO:3. The SEMA3C peptide may include at least 435 contiguous amino acids of the SEMA domain set out in SEQ ID NO:3. The SEMA3C peptide may include at least 440 contiguous amino acids of the SEMA domain set out in SEQ ID NO:3. The SEMA3C peptide may include at least 445 contiguous amino acids of the SEMA domain set out in SEQ ID NO:3. The SEMA3C peptide may include at least 450 contiguous amino acids of the SEMA domain set out in SEQ ID NO:3. The SEMA3C peptide may include at least 455 contiguous amino acids of the SEMA domain set out in SEQ ID NO:3. The SEMA3C peptide may include at least 460 contiguous amino acids of the SEMA domain set out in SEQ ID NO:3. The SEMA3C peptide may include at least 465 contiguous amino acids of the SEMA domain set out in SEQ ID NO:3. The SEMA3C peptide may include at least 470 contiguous amino acids of the SEMA domain set out in SEQ ID NO:3. The SEMA3C peptide may include at least 475 contiguous amino acids of the SEMA domain set out in SEQ ID NO:3.

The SEMA3C peptide may include at least 480 contiguous amino acids of the SEMA domain set out in SEQ ID NO:3. The SEMA3C peptide may include at least 485 contiguous amino acids of the SEMA domain set out in SEQ ID NO:3. The SEMA3C peptide may include at least 490 contiguous amino acids of the SEMA domain set out in SEQ ID NO:3. The SEMA3C peptide may include at least 495 contiguous amino acids of the SEMA domain set out in SEQ ID NO:3. The SEMA3C peptide may include the entire SEMA domain as set out in SEQ ID NO:3. Alternatively, the SEMA3C peptide may include a peptide having at least 80% identity to SEQ ID NO:3 and having SEMA3C inhibitory activity, or having a sequence substantially similar to SEQ ID NO:3 or a fragment thereof as set out above and having SEMA3C inhibitory activity.

The androgen deprivation therapy may include administering a luteinizing hormone-releasing hormone (LHRH) analog. The androgen deprivation therapy may include administering anti-androgen treatment. The androgen deprivation therapy may include administering an adrenal androgen inhibitor. The androgen deprivation therapy may be surgical. The androgen deprivation therapy and the SEMA3C inhibitor may be administered with one or more further therapeutic regimen(s). The therapeutic regimen may be a chemotherapeutic regimen. The therapeutic regimen may be a radiotherapeutic regimen.

In some embodiments, the sense strand of each interfering RNA independently comprises or consists of one or more of the sequences set forth in SEQ ID NOs: 2, 5-119. In related embodiments, the sense strand of each interfering RNA independently comprises or consists of at least about 15 contiguous nucleotides (e.g., at least 15, 16, 17, 18, or 19 contiguous nucleotides) of one or more of the sequences set forth in SEQ ID NOs: 2, 5-119. In particular embodiments, the sense strand of each interfering RNA may independently comprise or consist of from about 22 to about 28 nucleotides (e.g., 22, 23, 24, 25, 26, 27, or 28 nucleotides) in length. In certain instances, the sense strand of each interfering RNA has a modified (e.g., 2' OMe) and/or unmodified 3' overhang of 1, 2, 3, or 4 nucleotides, or is blunt ended at the 3' end. One of skill in the art will appreciate that the sense strand sequence may comprise or consist of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more additional nucleotides at the 5' and/or 3' end of one of the sequences described herein.

Provided herein are pharmaceutical compositions comprising one or a cocktail of RNAi (dsRNA) or antisense RNA (ssRNA) molecules that SEMA3C gene expression and a pharmaceutically acceptable carrier.

Delivery of a nucleic acid-lipid particle that targets SEMA3C gene expression may be accomplished with a lipid particle. The nucleic acid-lipid particle may comprise one or more unmodified and/or modified interfering RNA that silence SEMA3C gene expression, a cationic lipid, and a non-cationic lipid. In certain instances, the nucleic acid-lipid particle further comprises a conjugated lipid that inhibits aggregation of particles as known in the art. Alternatively, the nucleic acid-lipid particle comprises one or more unmodified and/or modified interfering RNA that silence SEMA3C gene expression, a cationic lipid, a non-cationic lipid, and a conjugated lipid that inhibits aggregation of particles.

DETAILED DESCRIPTION

Definitions

Figure 1:
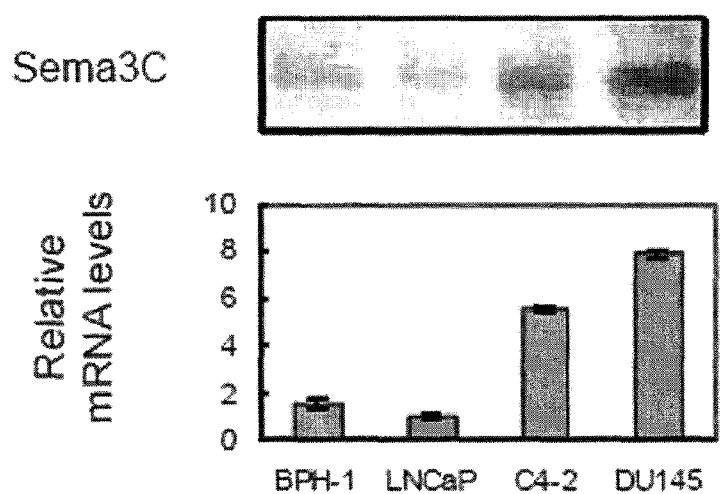
FIG. 1. shows a Western blot of SEMA3C protein and a bar graph of relative mRNA levels increased in hormone refractory C4-2 and DU145, but not androgen sensitive LNCaP and benign BPH-1 cells. Cells were cultured for 40 hours in 10% FBS media, and then cells were harvested and SEMA3C mRNA expression was determined by quantitative-PCR. Cell lysates were made following 6 hours of brefeldin A treatment and SEMA3C protein levels were determined by Western blotting.

"Systemic delivery," as used herein, may refer to delivery of lipid particles or other carriers that leads to a broad biodistribution of a SEMA3C inhibitor (such as an interfering RNA-RNAi (dsRNA); antisence RNA (ssRNA); anti-bodies (for example, MAbs or humanized MAbs, intrabodies, or fragments thereof; or a peptide) within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of SEMA3C can be by any means known in the art including, for example, intravenous, subcutaneous, and intraperitoneal. In an embodiment, systemic delivery of SEMA3C is by intravenous delivery.

"Local delivery," as used herein, refers to delivery of a SEMA3C inhibitor (such as an interfering RNA-RNAi (dsRNA); antisence RNA (ssRNA); anti-bodies (for example, MAbs or humanized MAbs), intrabodies, or fragments thereof; or a peptide) directly to a target site within an organism. For example, a SEMA3C inhibitor can be locally delivered by direct injection into a disease site, other target site, or a target organ such as the prostate.

As used herein, an "inhibitor" refers to an agent that restrains, retards, or otherwise causes inhibition of a physiological, chemical or enzymatic action or function. An inhibitor may cause at least 5% decrease in enzyme activity. An inhibitor may also refer to a drug, compound or agent that prevents or reduces the expression, transcription or translation of a gene or protein. An inhibitor may reduce or prevent the function of a protein, for instance by binding to and/or activating/inactivating another protein or receptor. An inhibitor may reduce or prevent the interaction of an enzyme or protein with another enzyme or protein. An inhibitor may cause degradation or clearance of a protein from a cell or from the body of a subject. For instance, an inhibitor may bind to the protein and such binding may target the protein for cellular degradation or for clearance from the body. Such an inhibitor could be an antibody, another protein or peptide or fragment thereof, another molecule (small molecule), a nucleic acid (RNA, DNA, PNA), etc. Binding of an inhibitor to the SEMA3C protein in view may prevent it from binding its cognate receptor, could prevent other important molecular interactions, or could alter the conformation of the protein. Binding of an inhibitor to the receptor of the protein may also prevent interaction of the protein with the receptor, and would thus also inhibit the cellular function of the protein in question. All such embodiments are considered within the definition of an inhibitor and are considered to be within the scope of the present invention.

The term "SEMA3C inhibitor" refers to any molecule that inhibit the SEMA3C protein, either directly or indirectly, for example by interfering with the SEMA3C activity, up regulating endogenous inhibitors and/or shutting down transcription of the SEMA3C gene or translation of the SEMA3C transcript. DNA or RNA may be used to inhibit the SEMA3C protein directly (via aptamers) or the transcription/translation of SEMA3C. SEMA3C inhibitors include, but are not limited to, peptides, antibodies (for example, polyclonal; monoclonal, or a fragment thereof (such as a F(ab')2 or Fab fragment), single chain Fc region (scFc), and intrabodies), interference RNA (RNAi), antisense molecules (such as antisense RNA and other nucleic acid molecules), small molecules (for example, Zinc00163599 (2-bromo-N-(2-methoxyphenyl) propanamide)), peptidomimetics etc. The SEMA3C inhibitor may further comprise a carrier to facilitate delivery and/or targeting of the SEMA3C inhibitor to the prostate.

siRNAs (one type of RNAi) are commercially available from numerous suppliers. For example, from Applied Biosystems (siRNA ID s20600 Pre-designed Inventoried 4427037; s20598 Pre-designed Inventoried 4427037; s20599 Pre-designed Inventoried 4427037), INVITROGEN (SEMA3C Stealth RNAi™ siRNA HSS116131; SEMA3C Stealth RNAi™ siRNA HSS116132; SEMA3C Stealth RNAi™ siRNA HSS116133), and ORIGENE (TF309560 pRFP-C—RS (vector) HuSH 29mer shRNA Constructs against SEMA3C; TG309560 pGFP-V-RS (vector) HuSH 29mer shRNA Constructs against SEMA3C; and TR309560 pRS (vector) HuSH 29mer shRNA Constructs against SEMA3C).

Anti-SEMA3C antibodies are commercially available from numerous suppliers. For example, from R&D Systems (Mouse Semaphorin 3C MAb (Clone 238835), Rat IgG2A WB MAB1728), Abcam plc (Semaphorin 3c antibody (ab39300) is a rabbit polyclonal made to a synthetic peptide conjugated to KLH derived from within residues 700 to the C-terminus of Human Semaphorin 3c), and Santa Cruz Biotechnology (rabbit polyclonal antibody made to an epitope corresponding to amino acids 592-751 mapping at the C-terminus of SEMA3C precursor of human origin SEMA3C(H-160) catalog #sc-33786). The monoclonal antibody from R&D Systems detects both mouse and human SEMA3C.

Alternatively, RNAi, and antisense RNA may be designed and made by methods known in the art. Similarly, antibodies may be designed and made by methods known in the art.

An antisense RNA or RNAi may be selected from any contiguous 19-50 nucleotide fragment of SEQ ID NO:4, such as AUGGCAUUCCGGACAAUUUG (SEQ ID NO: 2) or any one or more of the sequences set out in Table 2 (SEQ ID NOs: 5-119).

The term "aptamer", refers to nucleic acid molecules or peptide molecules that are capable of binding to a specific target molecule. Aptamers may be chosen from a large random sequence pool or from a subset of specific sequences. However, natural aptamers also exist in riboswitches.

The term "intrabodies", refer to intracellular antibodies, that act within a cell to bind to an intracellular target protein. Delivery of an intrabody may be the result of expression of the antibody within a target cell (for example via gene therapy). Methods for engineering intrabodies are known in the art (Marasco W A. Gene Ther. (1997) "Intrabodies: turning the humoral immune system outside in for intracellular immunization." 4(1):11-5), including the use of single-chain antibodies (scFvs), modification of immunoglobulin VL domains for hyperstability, selection of antibodies resistant to the more reducing intracellular environment, or expression as a fusion protein with maltose binding protein or other stable intracellular proteins.

The term "small hairpin RNA" or "short hairpin RNA" (shRNA) refers to a sequence of RNA having a hairpin turn that can be used to silence gene expression through RNA interference. shRNA may be introduced to a cell or cells in a vector. A U6 promoter may be used to ensure that the shRNA is expressed. A vector containing the shRNA may be passed on to progeny cells, which can provided inherited gene silencing. The shRNA hairpin structure may be cleaved by the cellular machinery to form "small interfering RNA" (siRNA), which is then bound to the RNA-induced silencing complex (RISC). The RISC complex is capable of binding to and cleaving mRNAs to which the siRNA is bound. The design and methods for making interfering RNAs (for example, siRNA, sisiRNA, tsiRNA, RNA-DNA chimeric duplex, tkRNA, Dicer-substrate dsRNA, shRNA, tRNA-shRNA, aiRNA, pre-miRNA, pri-miRNA mimic, pri-miRNA mimic cluster, transcriptional gene silencing (TGS), and combinations thereof) are well known in the art (For example, McIntyre, G J. and Fanning, G C. BMC Biotechnol. (2006) δ: 1; Paddison P. et al. Genes and Development (2002) 16 (8): 948-58; Yi R. et al. Genes & Development (2003) 17 (24): 3011-3016; Elbashir S. et al. Genes Dev (2001) 15 (2): 188-200; Zamore P. et al. Cell (2000) 101 (1): 25-33; Henschel A. et al Nucleic Acids Res. (2004) 32 (Web Server issue):W113-20 "DEQOR: a web-based tool for the design and quality control of siRNAs"; Sibley C R. et al. Molecular Therapy (2010) 18 (3):466-476).

As used herein a "subject" refers to an animal, such as a bird or a mammal. Specific animals include rat, mouse, dog, cat, cow, sheep, horse, pig or primate. A subject may further be a human, alternatively referred to as a patient. A subject may further be a transgenic animal. A subject may further be a rodent, such as a mouse or a rat.

As previously described, SEMA3C is a member of the semaphorin protein family. As used herein, SEMA3C', alternately referred to as 'semaphorin 3C' refers to the gene product of the semaphorin 3C gene. The human homologue of this gene is represented by EntrezGene #10512, and the associated GenBank protein accession number is Q99985.2 (SEQ ID NO:1). The *Mus musculus* SEMA3C is represented by EntrezGene #20348, Genbank protein accession number Q62181.1. Other SEMA3C homologues will be apparent to one of skill in the art. Semaphorins are typically characterized by distinctive structural and functional elements called 'SEMA domains' (Gherardi et al).

RNA may be single stranded, double stranded, synthetic, isolated, partially isolated, essentially pure or recombinant. RNA compounds may be naturally occurring, or they may be altered such that they differ from naturally occurring RNA compounds. Alterations may include addition, deletion, substitution or modification of existing nucleotides. Such nucleotides may be either naturally occurring, or non-naturally occurring nucleotides. Alterations may also involve addition of non-nucleotide material, for instance at the end or ends of an existing RNA compound, or at a site that is internal to the RNA compound (i.e. at one or more nucleotides).

The RNA compounds of the invention are capable of target-specific modulation of gene expression and typically exert their effect either by mediating degradation of the mRNA products of the target gene, or by preventing protein translation from the mRNA of the target gene. Such RNA compounds may thus also be referred to as 'RNA interference compounds'. The overall effect of interference with mRNA function is modulation of expression of the product of a target gene. In the context of this invention, 'modulation' means either inhibition or stimulation—i.e. either a decrease or an increase in expression. This modulation can be measured in ways which are routine in the art, for example by Northern blot assay or reverse transcriptase PCR of mRNA expression, Western blot or ELISA assay of protein expression, or by immunoprecipitation assay of protein expression. Effects on cell proliferation, cell viability or tumor growth can also be measured.

Antisense RNA compounds are typically single stranded RNA compounds which bind to complementary RNA compounds, such as target mRNA molecules, and block translation from the complementary RNA compounds by sterically interfering with the normal translational machinery. This process may be passive, in that it does not require or involve additional enzymes to mediate the RNA interference process. Specific targeting of antisense RNA compounds to inhibit the expression of a desired gene may generally involve designing the antisense RNA compound to have a homologous, complementary sequence to the desired gene. Perfect homology is not necessary for the RNA interference effect. In one embodiment, the antisense RNA compounds include any RNA compound with sufficient complementary homology to SEMA3C to bind to the SEMA3C mRNA transcript causing a reduction in translation of SEMA3C protein.

RNA compounds may be interfering RNA (RNAi) compounds. Typically, RNAi's, such siRNA compounds are short double stranded RNA compounds between 4 and 50 nucleotides in length. Alternatively, siRNA compounds are between 16 to 29 nucleotides in length, even more preferably between 18 to 23 nucleotides in length and most preferably between 21-23 nucleotides in length. The siRNA compounds may include short nucleotide 'overhangs' on each end, which are single stranded extensions which are not paired with a complementary base on the opposite strand. Alternatively, the overhangs would be on the 3' end of each strand of the siRNA compound, and are typically 1-3 nucleotides in length. The siRNA compounds of the present invention may be synthesized as individual strands which are subsequently annealed to produce the double stranded siRNA compound. Alternately, the siRNA compounds may derived from a short hairpin RNA (shRNA) molecule, or from a longer RNA compound, which has been processed by the cellular enzyme called dicer, which processes the longer RNA compounds to produce siRNA compounds. Generally, siRNA compounds mediate RNA interference via an enzyme-dependent process in which the target mRNA is degraded, such that it can no longer be translated into its associated protein product. Not being bound by theory, the double stranded siRNA compounds are separated into single stranded molecules and integrated into an activated 'RISC complex'. After integration into the RISC, siRNAs base-pair to their target mRNA and induce cleavage of the mRNA, thereby preventing it from being used as a translation template.

Design of gene specific antisense RNA and RNAi compounds, including nucleotide sequence selection and additionally appropriate alterations, would be known to one of skill in the art and as described herein. Examples of SEMA3C RNA's may be found in SEQ ID No: 2 and Table 2 (SEQ ID Nos: 5-119). Specific targeting of siRNA compounds to modulate expression of a desired gene is generally related to the degree of homology between the siRNA compound and the target gene. Design features to optimize the efficacy and specificity of an antisense RNA compound may depend on the specific sequence chosen for the design of the RNA compound. Numerous examples of methods for designing and optimizing antisense RNA compounds are found in the journal literature—i.e. (Pan and Clawson 2006; Patzel 2007; Peek and Behlke 2007). There are also many computer based tools for designing antisense RNA compounds, which may, for instance, use algorithms or other rule-based formulae to determine optimal antisense RNA compounds. It would thus be within the skill of one in the art to design a large number of different antisense RNA compounds which would be expected to inhibit a target gene. Exact sequence complementarity is not necessary for the siRNA compound to modulate expression of the target gene. In some embodiments, the antisense RNA compounds include any RNA compounds which bear sequence homology to the SEMA3C gene and which are capable of modulating the expression of SEMA3C protein. Provided herein are non-limiting examples of RNA compounds which modulate the expression of SEMA3C and are thus SEMA3C inhibitors. The SEMA3C inhibitors described herein may also be DNA interference compounds. Such compounds have properties similar to RNA interference compounds, as described in the art.

The terms "peptide", "polypeptide" and "protein" may be used interchangeably, and refer to a compound comprised of at least two amino acid residues covalently linked by peptide bonds or modified peptide bonds, for example peptide isosteres (modified peptide bonds) that may provide additional desired properties to the peptide, such as increased half-life. A peptide may comprise at least two amino acids. The amino acids comprising a peptide or protein described herein may also be modified either by natural processes, such as posttranslational processing, or by chemical modification techniques which are well known in the art. Modifications can occur anywhere in a peptide, including the peptide backbone, the amino acid side-chains and the amino or carboxyl termini. It is understood that the same type of modification may be present in the same or varying degrees at several sites in a given peptide.

Examples of modifications to peptides may include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins-Structure and Molecular Properties, 2$^{nd}$ ed., T. E. Creighton, W. H. Freeman and Company, New York, 1993 and Wold F, Posttranslational Protein Modifications: Perspectives and Prospects, pgs. 1-12 in Posttranslational Covalent Modification of Proteins, B. C. Johnson, ed., Academic Press, New York, 1983; Seifter et al., Analysis for protein modifications and nonprotein cofactors, Meth. Enzymol. (1990) 182: 626-646 and Rattan et al. (1992), Protein Synthesis: Posttranslational Modifications and Aging," Ann NY Acad Sci 663: 48-62.

A "substantially similar sequence" refers to an amino acid sequence that differs from a reference sequence only by one or more substitutions, but which may, for example, be functionally homologous to another substantially similar sequence. It will be appreciated by a person of skill in the art the aspects of the individual amino acids in a peptide of the invention that may be substituted.

Amino acid sequence similarity or identity may be computed by using the BLASTP and TBLASTN programs which employ the BLAST (basic local alignment search tool) 2.0 algorithm. Techniques for computing amino acid sequence similarity or identity are well known to those skilled in the art, and the use of the BLAST algorithm is described in ALTSCHUL et al. 1990, J Mol. Biol. 215: 403-410 and ALTSCHUL et al. (1997), Nucleic Acids Res. 25: 3389-3402.

Amino acids may be described as, for example, polar, non-polar, acidic, basic, aromatic or neutral. A polar amino acid is an amino acid that may interact with water by hydrogen bonding at biological or near-neutral pH. The polarity of an amino acid is an indicator of the degree of hydrogen bonding at biological or near-neutral pH. Examples of polar amino acids include serine, proline, threonine, cysteine, asparagine, glutamine, lysine, histidine, arginine, aspartate, tyrosine and glutamate. Examples of non-polar amino acids include glycine, alanine, valine leucine, isoleucine, methionine, phenylalanine, and tryptophan. Acidic amino acids have a net negative charge at a neutral pH. Examples of acidic amino acids include aspartate and glutamate. Basic amino acids have a net positive charge at a neutral pH. Examples of basic amino acids include arginine, lysine and histidine. Aromatic amino acids are generally nonpolar, and may participate in hydrophobic interactions. Examples of aromatic amino acids include phenylalanine, tyrosine and tryptophan. Tyrosine may also participate in hydrogen bonding through the hydroxyl group on the aromatic side chain. Neutral, aliphatic amino acids are generally nonpolar and hydrophobic. Examples of neutral amino acids include alanine, valine, leucine, isoleucine and methionine. An amino acid may be described by more than one descriptive category. Amino acids sharing a common descriptive category may be substitutable for each other in a peptide.

Nomenclature used to describe the peptide compounds of the present invention follows the conventional practice where the amino group is presented to the left and the carboxy group to the right of each amino acid residue. In the sequences representing selected specific embodiments of the present invention, the amino- and carboxy-terminal groups, although not specifically shown, will be understood to be in the form they would assume at physiologic pH values, unless otherwise specified. In the amino acid structure formulae, each residue may be generally represented by a one-letter or three-letter designation, corresponding to the trivial name of the amino acid, in accordance with Table 1.

TABLE 1

Nomenclature and abbreviations of the 20 standard L-amino acids commonly found in naturally occurring peptides.

| Full name | Three-letter abbreviation | One-letter abbreviation |
|---|---|---|
| Alanine | Ala | A |
| Cysteine | Cys | C |
| Aspartic acid | Asp | D |
| Glutamic acid | Glu | E |
| Phenylalanine | Phe | F |
| Glycine | Gly | G |
| Histidine | His | H |
| Isoleucine | Ile | I |
| Lysine | Lys | K |
| Leucine | Leu | L |
| Methionine | Met | M |
| Asparagine | Asp | N |
| Proline | Pro | P |
| Glutamine | Gln | Q |
| Arginine | Arg | R |
| Serine | Ser | S |
| Threonine | Thr | T |
| Valine | Val | V |
| Tryptophan | Trp | W |
| Tyrosine | Tyr | T |

The hydropathy index of an amino acid is a scale indicating the tendency of an amino acid to seek out an aqueous environment (negative value) or a hydrophobic environment (positive value) (KYTE & DOOLITTLE 1982. J Mol Biol 157:105-132). Hydropathy indices of the standard amino acids include alanine (1.8), arginine (−4.5), asparagine (−3.5), aspartic acid (−3.5), cysteine (2.5), glutamine (−3.5), glutamic acid (−3.5), glycine (−0.4), histidine (−3.2), isoleucine (4.5), leucine (3.8), lysine (−3.9), methionine (1.9), phenylalanine (2.8), proline (−1.6), serine (−0.8), threonine (−0.7), tryptophan (−0.9), tyrosine (−1.3), and valine (4.2). Amino acids with similar hydropathy indices may be substitutable for each other in a peptide.

In order to further exemplify what is meant by a conservative amino acid substitution, Groups A-F are listed below. The replacement of one member of the following groups by another member of the same group is considered to be a conservative substitution.

Group A includes leucine, isoleucine, valine, methionine, phenylalanine, serine, cysteine, threonine, and modified amino acids having the following side chains: ethyl, isobutyl, —CH$_2$CH$_2$OH, —CH$_2$CH$_2$CH$_2$OH, —CH$_2$CHOHCH$_3$ and CH$_2$SCH$_3$.

Group B includes glycine, alanine, valine, serine, cysteine, threonine, and a modified amino acid having an ethyl side chain.

Group C includes phenylalanine, phenylglycine, tyrosine, tryptophan, cyclohexylmethyl, and modified amino residues having substituted benzyl or phenyl side chains.

Group D includes glutamic acid, aspartic acid, a substituted or unsubstituted aliphatic, aromatic or benzylic ester of glutamic or aspartic acid (e.g., methyl, ethyl, n-propyl, iso-propyl, cyclohexyl, benzyl, or substituted benzyl), glutamine, asparagine, CO—NH-alkylated glutamine or asparagine (e.g., methyl, ethyl, n-propyl, and iso-propyl), and modified amino acids having the side chain —(CH2)3COOH, an ester thereof (substituted or unsubstituted aliphatic, aromatic, or benzylic ester), an amide thereof, and a substituted or unsubstituted N-alkylated amide thereof.

Group E includes histidine, lysine, arginine, N-nitroarginine, p-cycloarginine, g-hydroxyarginine, N-amidinocitruline, 2-amino guanidinobutanoic acid, homologs of lysine, homologs of arginine, and ornithine.

Group F includes serine, threonine, cysteine, and modified amino acids having C1-C5 straight or branched alkyl side chains substituted with —OH or —SH.

Groups A-F are exemplary and are not intended to limit the invention.

Peptides or peptide analogues can be synthesised by chemical techniques known in the art, for example, by automated synthesis using solution or solid phase synthesis methodology. Automated peptide synthesisers are commercially available and use techniques well known in the art. Peptides and peptide analogues can also be prepared using recombinant DNA technology using methods such as those described in, for example, SAMBROOK J. AND RUSSELL D. (2000) Molecular Cloning: A Laboratory Manual (Third Edition) Cold Spring Harbor Laboratory, Cold Spring Harbor Laboratory Press, Cold Spring Harbor, N.Y.) or AUSUBEL et al. (Current Protocols in Molecular Biology, John Wiley & Sons, 1994).

A "peptidomimetic" is a compound comprising non-peptidic structural elements that mimics the biological action of a parent peptide. A peptidomimetic may not have classical peptide characteristics such as an enzymatically scissile peptidic bond. A parent peptide may initially be identified as a binding sequence or phosphorylation site on a protein of interest, or may be a naturally occurring peptide, for example a peptide hormone. Assays to identify peptidomimetics may include a parent peptide as a positive control for comparison purposes, when screening a library, such as a peptidomimetic library. A peptidomimetic library is a library of compounds that may have biological activity similar to that of a parent peptide.

Amino acids contained within the peptides described herein will be understood to be in the L- or D-configuration. In peptides and peptidomimetics of the present invention, D-amino acids may be substitutable for L-amino acids. Amino acids contained within the peptides of the present invention, and particularly at the carboxy- or amino-terminus, may be modified by methylation, amidation, acetylation or substitution with other chemical groups which may change the circulating half-life of the peptide without adversely affecting their biological activity. Additionally, a disulfide linkage may be present or absent in the peptides of the invention. Another approach for modification of an existing sequence is to synthesize the corresponding retro-inverso version. A retro-inverso peptide is one in which the sequence is reversed ie. reversal of the N to C terminal and synthesized using D-amino acids. Retro inverso analogs of L peptides when aligned alongside each other from N to C and C to N have all side chains in the same orientation, however the peptide bonds are reversed and sterically unavailable for cleavage by proteases. Nair et. al. 2003 *J. Immunol.* 170: 1362-1373.

"Peptide nucleic acids" (PNA) as used herein refer to modified nucleic acids in which the sugar phosphate skeleton of a nucleic acid has been converted to an N-(2-aminoethyl)-glycine skeleton. Although the sugar-phosphate skeletons of DNA/RNA are subjected to a negative charge under neutral conditions resulting in electrostatic repulsion between complementary chains, the backbone structure of PNA does not inherently have a charge. Therefore, there is no electrostatic repulsion. Consequently, PNA has a higher ability to form double strands as compared with conventional nucleic acids, and has a high ability to recognize base sequences. Furthermore, PNAs are generally more robust than nucleic acids. PNAs may also be used in arrays and in other hybridization or other reactions as described above and herein for oligonucleotides.

As used herein, the term "vector" refers to a polynucleotide compound used for introducing exogenous or endogenous polynucleotide into host cells. A vector comprises a nucleotide sequence, which may encode one or more polypeptide molecules. Plasmids, cosmids, viruses and bacteriophages, in a natural state or which have undergone recombinant engineering, are non-limiting examples of commonly used vectors to provide recombinant vectors comprising at least one desired isolated polynucleotide molecule.

The nucleic acid molecules can be inserted into any suitable vector. Suitable vectors include, without limitation, viral vectors. Suitable viral vectors include, without limitation, retroviral vectors, alphaviral, vaccinial, adenoviral, adenoassociated viral, herpes viral, and fowl pox viral vectors. The vectors preferably have a native or engineered capacity to transform eukaryotic cells, e.g., CHO-K1 cells. Additionally, the vectors useful in the context of the invention can be "naked" nucleic acid vectors (i.e., vectors having little or no proteins, sugars, and/or lipids encapsulating them) such as plasmids or episomes, or the vectors can be complexed with other molecules. Other molecules that can be suitably combined with the inventive nucleic acids include without limitation viral coats, cationic lipids, liposomes, polyamines, gold particles, and targeting moieties such as ligands, receptors, or antibodies that target cellular molecules.

Nonstandard amino acids may occur in nature, and may or may not be genetically encoded. Examples of genetically encoded nonstandard amino acids include selenocysteine, sometimes incorporated into some proteins at a UGA codon, which may normally be a stop codon, or pyrrolysine, sometimes incorporated into some proteins at a UAG codon, which may normally be a stop codon. Some nonstandard amino acids that are not genetically encoded may result from modification of standard amino acids already incorporated in a peptide, or may be metabolic intermediates or precursors, for example. Examples of nonstandard amino acids include 4-hydroxyproline, 5-hydroxylysine, 6-N-methyllysine, gamma-carboxyglutamate, desmosine, selenocysteine, ornithine, citrulline, lanthionine, 1-aminocyclopropane-1-carboxylic acid, gamma-aminobutyric acid, carnitine, sarcosine, or N-formylmethionine. Synthetic variants of standard and nonstandard amino acids are also known and may include chemically derivatized amino acids, amino acids labeled for identification or tracking, or amino acids with a variety of side groups on the alpha carbon. Examples of such side groups are known in the art and may include aliphatic, single aromatic, polycyclic aromatic, heterocyclic, heteronuclear, amino, alkylamino, carboxyl, carboxamide, carboxyl ester, guanidine, amidine, hydroxyl, alkoxy, mercapto-, alkylmercapto-, or other heteroatom-containing side chains. Other synthetic amino acids may include alpha-imino acids, non-alpha amino acids such as beta-amino acids, des-carboxy or des-amino acids. Synthetic variants of amino acids may be synthesized using general methods known in the art, or may be purchased from commercial suppliers, for example RSP Amino Acids LLC (Shirley, Mass.).

The term "antibody" as used herein refers to immune system proteins, also called immunoglobulins, produced in response to foreign substances (antigens). Antibodies typically contain two heavy chains and two light chains, which are joined. Variability in the structure of these chains provides antigen specificity—ie. allows individual antibodies to recognize specific antigens. The term antibody may include polyclonal and monoclonal antibodies, chimeric, single chain, or humanized antibodies, as well as Fab or F(ab)$^2$ fragments, including the products of an Fab or other immunoglobulin expression library. Methods of making such antibodies or fragments are known in the art and may be found in, for example HARLOW, E and LANE D. Antibodies: A Laboratory Manual. 1988. Cold Spring Harbor Laboratory Press. Antibodies according to some embodiments of the invention may also be intracellular antibodies, sometimes referred to as 'intrabodies'. Methods for designing, making and/or using such antibodies has been described in the art, for instance (Lecerf et al. 2001; Hudson and Souriau 2003). The use of intracellular antibodies has been suggested as a potential strategy for therapeutic targeting of protein misfolding diseases (Cardinale and Biocca 2008). Selection or identification of specific peptides for use as epitopes for production of antibodies that differentiate between proteins, or isoforms of proteins may be made using sequence comparisons—one of skill in the art will be able to identify suitable peptide or protein sequences that may be useful for producing antibodies with the desired selectivities. Polyclonal antibodies are antibodies that are derived from different B-cell lines. They are a mixture of immunoglobulin molecules secreted against a specific antigen, each recognising a different epitope. These antibodies are typically produced by immunization of a suitable mammal, such as a mouse, rabbit or goat. Larger mammals are often preferred as the amount of serum that can be collected is greater. An antigen is injected into the mammal. This induces the B-lymphocytes to produce IgG immunoglobulins specific for the antigen. This IgG is purified from the mammal's serum. By contrast, monoclonal antibodies are derived from a single cell line. Adjuvants may be used to improve or enhance an immune response to antigens. In certain embodiments of the present invention, there are provided antibodies or intrabodies raised against or that bind to the peptides of the present invention. Also provided are methods of use of such antibodies or intrabodies.

The monoclonal antibodies referenced herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567). Chimeric antibodies of interest herein include "primatized" antibodies comprising variable domain antigen-binding sequences derived from a non-human primate (e.g., Old World Monkey or Ape) and human constant region sequences.

"Antibody-dependent cell-mediated cytotoxicity" (ADCC) refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express Fc.γ.RIII only, whereas monocytes express FcγRI, FcγRII and FcγRIII. To assess ADCC activity of a molecule of interest, an in vitro ADCC assay may be performed (U.S. Pat. Nos. 5,003,621; 5,821,337). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al PNAS (USA), 95:652-656 (1998).

An antibody which "induces cell death" is one which causes a viable cell to become nonviable. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody is able to induce cell death, loss of membrane integrity as evaluated by uptake of propidium iodide (PI), trypan blue or 7AAD can be assessed relative to untreated cells. Cell death-inducing antibodies are those which induce PI uptake in the PI uptake assay in BT474 cells.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies).

The SEMA3C inhibitors described herein may be in isolation, or may be linked to or in combination with tracer compounds, liposomes, carbohydrate carriers, polymeric carriers or other agents or excipients as will be apparent to one of skill in the art. In an alternate embodiment, such compounds may comprise a medicament, wherein such compounds may be present in a pharmacologically effective amount.

The term "medicament" as used herein refers to a composition that may be administered to a patient or test subject and is capable of producing an effect in the patient or test subject. The effect may be chemical, biological or physical, and the patient or test subject may be human, or a non-human animal, such as a rodent or transgenic mouse, or a dog, cat, cow, sheep, horse, hamster, guinea pig, rabbit or pig. The medicament may be comprised of the effective chemical entity alone or in combination with a pharmaceutically acceptable excipient.

The term "pharmaceutically acceptable excipient" may include any and all solvents, dispersion media, coatings, antibacterial, antimicrobial or antifungal agents, isotonic and absorption delaying agents, and the like that are physiologically compatible. An excipient may be suitable for intravenous, intraperitoneal, intramuscular, subcutaneous, intrathecal, topical or oral administration. An excipient may include sterile aqueous solutions or dispersions for extemporaneous preparation of sterile injectable solutions or dispersion. Use of such media for preparation of medicaments is known in the art.

SEMA3C inhibitors described herein may be administered in any of a variety of known routes. Examples of methods that may be suitable for the administration of SEMA3C inhibitors described herein include orally, intravenous, inhalation, intramuscular, subcutaneous, topical, intraperitoneal, intra-rectal or intra-vaginal suppository, sublingual, and the like. SEMA3C inhibitors described herein may be administered as a sterile aqueous solution, or may be administered in a fat-soluble excipient, or in another solution, suspension, patch, tablet or paste format as is appropriate. A composition comprising the SEMA3C inhibitors described herein may be formulated for administration by inhalation. For instance, a SEMA3C inhibitors described herein may be combined with an excipient to allow dispersion in an aerosol. Examples of inhalation formulations will be known to those skilled in the art. Other agents may be included in combination with the SEMA3C inhibitors described herein to aid uptake or metabolism, or delay dispersion within the host, such as in a controlled-release formulation. Examples of controlled release formulations will be known to those of skill in the art, and may include microencapsulation, embolism within a carbohydrate or polymer matrix, and the like. Other methods known in the art for making formulations are found in, for example, "Remington's Pharmaceutical Sciences", (19th edition), ed. A. Gennaro, 1995, Mack Publishing Company, Easton, Pa.

The dosage of SEMA3C inhibitors described herein may vary depending on the route of administration (oral, intravenous, inhalation, or the like) and the form in which the composition or compound is administered (solution, controlled release or the like). Determination of appropriate dosages is within the ability of one of skill in the art. As used herein, an "effective amount", a "therapeutically effective amount", or a "pharmacologically effective amount" of a medicament refers to an amount of a medicament present in such a concentration to result in a therapeutic level of drug delivered over the term that the drug is used. This may be dependent on mode of delivery, time period of the dosage, age, weight, general health, sex and diet of the subject receiving the medicament. Methods of determining effective amounts are known in the art. It is understood that it could be potentially beneficial to restrict delivery of the SEMA3C inhibitors described herein to the target tissue or cell in which inhibition of SEMA3C is desired. It is also understood that it may be desirable to target SEMA3C inhibitors described herein to a desired tissue or cell type. The SEMA3C SEMA3C inhibitors described herein of the invention may be coupled to a cell uptake moiety. The targeting moiety may also function as the cell uptake moiety.

Delivery of bioactive molecules such as peptides, to a cell or cells in a reasonably efficient manner may require more than just the 'dumping' of the naked peptide onto the cell, or administering the naked peptide into the patient or test subject. Agents that enable delivery of bioactive molecules into cells in a suitable manner so as to provide an effective amount, such as a pharmacologically effective amount are known in the art, and are described in, for example, DIETZ et al 2004. *Mol. Cell. Neurosci* 27:85-131. Examples of such agents include liposomes, lipid particles, antibodies or receptor ligands that may be coupled to the bioactive molecule, viral vectors, and protein transduction domains (PTD). Examples of PTDs include Antennapedia homeodomain (PEREZ et al 1992 *J. Cell Sci* 102:717-722), transportan (POOGA et al 1998 *FASEB J* 12: 67-77), the translocation domains of diphtheria toxin (STENMARK et al 1991 *J Cell Biol* 113:1025-1032; WIEDLOCHA et al 1994 *Cell* 76:1039-1051), anthrax toxin (BALLARD et al 1998 *Infect. Immun* 66:615-619; BLANKE et al 1996 *Proc Natl Acad Sci* 93: 8437-8442) and *Pseudomonas* exotoxin A (PRIOR et al 1992 *Biochemistry* 31:3555-3559), protegrin derivatives such as dermaseptin S4 (HARITON-GAZAL et al 2002 *Biochemistry* 41:9208-9214), HSV-1 VP22 (DILBER et al 1999 *Gene Ther.* 6:12-21), PEP-1 (MORRIS et al 2001 *Nature Biotechnol* 19:1173-1176), basic peptides such as poly-L and poly-D-lysine (WOLFERT et al 1996 *Gene Ther.* 3:269-273; RYSER et al 1980 *Cancer* 45:1207-1211; SHEN et al 1978 *Proc Natl Acad Sci* 75:1872-1876), HSP70 (FUJIHARA et al 1999 *EMBO J.* 18:411-419) and HIV-TAT (DEMARCHI et al 1996 *J Virol* 70:4427-4437). Other examples and related details of such protein transduction domains are described in DIETZ, supra and references therein.

As used herein, the term "cancer" refers to a proliferative disorder caused or characterized by the proliferation of cells which have lost susceptibility to normal growth control. The term cancer, as used in the present application, includes tumors and any other proliferative disorders, such as prostate adenocarcinoma. Cancers of the same tissue type usually originate in the same tissue, and may be divided into different subtypes based on their biological characteristics. Four general categories of cancers are carcinoma (epithelial tissue derived), sarcoma (connective tissue or mesodermal derived), leukemia (blood-forming tissue derived) and lymphoma (lymph tissue derived). Over 200 different types of cancers are known, and every organ and tissue of the body may be affected. Specific examples of cancers that do not limit the definition of cancer may include melanoma, leukemia, astrocytoma, glioblastoma, retinoblastoma, lymphoma, glioma, Hodgkins' lymphoma and chronic lymphocyte leukemia. Examples of organs and tissues that may be affected by various cancers include pancreas, breast, thyroid, ovary, uterus, testis, prostate, thyroid, pituitary gland, adrenal gland, kidney, stomach, esophagus, colon or rectum, head and neck, bone, nervous system, skin, blood, nasopharyngeal tissue, lung, urinary tract, cervix, vagina, exocrine glands and endocrine glands. Alternatively, a cancer may be multicentric or of unknown primary site (CUPS).

As used herein, a "cancerous cell" refers to a cell that has undergone a transformation event and whose growth is no longer regulated to the same extent as before said transformation event. A tumor refers to a collection of cancerous cells, often found as a solid or semi-solid lump in or on the tissue or a patient or test subject.

A cancer or cancerous cell may be described as "sensitive to" or "resistant to" a given therapeutic regimen or chemotherapeutic agent based on the ability of the regimen to kill cancer cells or decrease tumor size, reduce overall cancer growth (i.e. through reduction of angiogenesis), and/or inhibit metastasis. Cancer cells that are resistant to a therapeutic regimen may not respond to the regimen and may continue to proliferate. Cancer cells that are sensitive to a therapeutic regimen may respond to the regimen resulting in cell death, a reduction in tumor size, reduced overall growth (tumor burden) or inhibition of metastasis. For example, this desirably manifest itself in a reduction in tumor size, overall growth/tumor burden or the incidence of metastasis of about 10% or more, for example, about 30%, about 40%, about 50%, about 60%, about 70%, about 80%, or more, to about 2-fold, about 3-fold, about 4-fold, about 5-fold, about 10-fold, about 15-fold, about 20-fold or more. Monitoring of a response may be accomplished by numerous pathological, clinical and imaging methods as described herein and known to persons of skill in the art.

A common theme for a chemotherapeutic agent or combination of agents is to induce death of the cancerous cells. For example, DNA adducts such as nitrosoureas, busulfan, thiotepa, chlorambucil, cisplatin, mitomycin, procarbazine, or dacacarbazine slow. the growth of the cancerous cell by forcing the replicating cell to repair the damaged DNA before the M-phase of the cell cycle, or may by themselves cause sufficient damage to trigger apoptosis of the cancerous cell. Other events such as gene expression or transcription, protein translation, or methylation of the replicated DNA, for example, may also be interfered with by the varied arsenal of chemotherapeutic agents available to the clinician and help to trigger apoptotic processes within the cancerous cells. Alternately, a chemotherapeutic agent may enable the cancerous cell to be killed by aspects of the patient or test subject's humoral or acquired immune system, for example, the complement cascade or lymphocyte attack.

As used herein, a "therapeutic regimen" or "therapy" refers to the administration of at least one agent which is harmful to cancerous cells. Suitable therapeutic regimens for use in accordance with the invention include, but are not limited to, "chemotherapeutic regimens," "radiotherapeutic regimens," "alternative therapeutic regimen" and combinations thereof.

As used herein, a "chemotherapeutic regimen" or "chemotherapy" refers to the administration of at least one chemotherapy agent which is harmful to destroy cancerous cells. There are a myriad of such chemotherapy agents available to a clinician. Chemotherapy agents may be administered to a subject in a single bolus dose, or may be administered in smaller doses over time. A single chemotherapeutic agent may be used (single-agent therapy) or more than one agent may be used in combination (combination therapy). Chemotherapy may be used alone to treat some types of cancer. Alternatively, chemotherapy may be used in combination with other types of treatment, for example, radiotherapy or alternative therapies (for example immunotherapy) as described herein. Additionally, a chemosensitizer may be administered as a combination therapy with a chemotherapy agent.

As used herein, a "chemotherapeutic agent" refers to a medicament that may be used to treat cancer, and generally has the ability to kill cancerous cells directly. Examples of chemotherapeutic agents include alkylating agents, antimetabolites, natural products, hormones and antagonists, and miscellaneous agents. Examples of alternate names are indicated in brackets. Examples of alkylating agents include nitrogen mustards such as mechlorethamine, cyclophosphamide, ifosfamide, melphalan (L-sarcolysin) and chlorambucil; ethylenimines and methylmelamines such as hexamethylmelamine and thiotepa; alkyl sulfonates such as busulfan; nitrosoureas such as carmustine (BCNU), semustine (methyl-CCNU), lomustine (CCNU) and streptozocin (streptozotocin); DNA synthesis antagonists such as estramustine phosphate; and triazines such as dacarbazine (DTIC, dimethyl-triazenoimidazolecarboxamide) and temozolomide. Examples of antimetabolites include folic acid analogs such as methotrexate (amethopterin); pyrimidine analogs such as fluorouracin (5-fluorouracil, 5-FU, 5FU), floxuridine (fluorodeoxyuridine, FUdR), cytarabine (cytosine arabinoside) and gemcitabine; purine analogs such as mercaptopurine (6-mercaptopurine, 6-MP), thioguanine (6-thioguanine, TG) and pentostatin (2'-deoxycoformycin, deoxycoformycin), cladribine and fludarabine; and topoisomerase inhibitors such as amsacrine. Examples of natural products include vinca alkaloids such as vinblastine (VLB) and vincristine; taxanes such as paclitaxel and docetaxel (Taxotere); epipodophyllotoxins such as etoposide and teniposide; camptothecins such as topotecan and irinotecan; antibiotics such as dactinomycin (actinomycin D), daunorubicin (daunomycin, rubidomycin), doxorubicin, bleomycin, mitomycin (mitomycin C), idarubicin, epirubicin; enzymes such as L-asparaginase; and biological response modifiers such as interferon alpha and interlelukin 2. Examples of hormones and antagonists include luteinising releasing hormone agonists such as buserelin; adrenocorticosteroids such as prednisone and related preparations; progestins such as hydroxyprogesterone caproate, medroxyprogesterone acetate and megestrol acetate; estrogens such as diethylstilbestrol and ethinyl estradiol and related preparations; estrogen antagonists such as tamoxifen and anastrozole; androgens such as testosterone propionate and fluoxymesterone and related preparations; androgen antagonists such as flutamide and bicalutamide; and gonadotropin-releasing hormone analogs such as leuprolide. Examples of miscellaneous agents include thalidomide; platinum coordination complexes such as cisplatin (cis-DDP), oxaliplatin and carboplatin; anthracenediones such as mitoxantrone; substituted ureas such as hydroxyurea; methylhydrazine derivatives such as procarbazine (N-methylhydrazine, MIH); adrenocortical suppressants such as mitotane (o,p'-DDD) and aminoglutethimide; RXR agonists such as bexarotene; and tyrosine kinase inhibitors such as imatinib. Alternate names and trade-names of these and additional examples of chemotherapeutic agents, and their methods of use including dosing and administration regimens, will be known to a person versed in the art, and may be found in, for example "The Pharmacological basis of therapeutics", $10^{th}$ edition. HARDMAN H G., LIMBIRD L E. editors. McGraw-Hill, New York, and in "Clinical Oncology", $3^{rd}$ edition. Churchill Livingstone/Elsevier Press, 2004. ABELOFF, M D. editor. In particular, suitable chemotherapeutic agents for use in accordance with the invention include, without limitation, nanoparticle albumin-bound paclitaxels.

As used herein, the term "radiotherapeutic regimen" or "radiotherapy" refers to the administration of radiation to kill cancerous cells. Radiation interacts with various molecules within the cell, but the primary target, which results in cell death is the deoxyribonucleic acid (DNA). However, radiotherapy often also results in damage to the cellular and nuclear membranes and other organelles. DNA damage usually involves single and double strand breaks in the sugar-phosphate backbone. Furthermore, there can be cross-linking of DNA and proteins, which can disrupt cell function. Depending on the radiation type, the mechanism of DNA damage may vary as does the relative biologic effectiveness. For example, heavy particles (i.e. protons, neutrons) damage DNA directly and have a greater relative biologic effectiveness. Electromagnetic radiation results in indirect ionization acting through short-lived, hydroxyl free radicals produced primarily by the ionization of cellular water. Clinical applications of radiation consist of external beam radiation (from an outside source) and brachytherapy (using a source of radiation implanted or inserted into the patient). External beam radiation consists of X-rays and/or gamma rays, while brachytherapy employs radioactive nuclei that decay and emit alpha particles, or beta particles along with a gamma ray.

Radiotherapy may further be used in combination chemotherapy, with the chemotherapeutic agent acting as a radiosensitizer. The specific choice of radiotherapy suited to an individual patient may be determined by a skilled person at the point of care, taking into consideration the tissue and stage of the cancer. Examples of radiotherapy approaches to various cancers may be found in, for example "Clinical Oncology", $3^{rd}$ edition. Churchill Livingstone/Elsevier Press, 2004. ABELOFF, M D. editor.

As used herein, the term "alternative therapeutic regimen" or "alternative therapy" may include for example, biologic response modifiers (including polypeptide-, carbohydrate-, and lipid-biologic response modifiers), toxins, lectins, anti-angiogenic agents, receptor tyrosine kinase inhibitors (for example Iressa™ (gefitinib), Tarceva™ (erlotinib), Erbitux™ (cetuximab), imatinib mesilate (Gleevec™), proteosome inhibitors (for example bortezomib, Velcade™); VEGFR2 inhibitors such as PTK787 (ZK222584), aurora kinase inhibitors (for example ZM447439); mammalian target of rapamycin (mTOR) inhibitors, cyclooxygenase-2 (COX-2) inhibitors, rapamycin inhibitors (for example sirolimus, Rapamune™); farnesyltransferase inhibitors (for example tipifarnib, Zarnestra); matrix metalloproteinase inhibitors (for example BAY 12-9566; sulfated polysaccharide tecogalan); angiogenesis inhibitors (for example Avastin™ (bevacizumab); analogues of fumagillin such as TNP-4; carboxyaminotriazole; BB-94 and BB-2516; thalidomide; interleukin-12; linomide; peptide fragments; and antibodies to vascular growth factors and vascular growth factor receptors); platelet derived growth factor receptor inhibitors, protein kinase C inhibitors, mitogen-activated kinase inhibitors, mitogen-activated protein kinase kinase inhibitors, Rous sarcoma virus transforming oncogene (SRC) inhibitors, histonedeacetylase inhibitors, small hypoxia-inducible factor inhibitors, hedgehog inhibitors, and TGF-β signalling inhibitors. Furthermore, an immunotherapeutic agent would also be considered an alternative therapeutic regimen. Examples include chemokines, chemotaxins, cytokines, interleukins, or tissue factor. Suitable immunotherapeutic agents also include serum or gamma globulin containing preformed antibodies; nonspecific immunostimulating adjuvants; active specific immunotherapy; and adoptive immunotherapy. In addition, alternative therapies may include other biological-based chemical entities such as polynucleotides, including antisense molecules, polypeptides, antibodies, gene therapy vectors and the like. Such alternative therapeutics may be administered alone or in combination, or in combination with other therapeutic regimens described herein. Alternate names and trade-names of these agents used in alternative therapeutic regimens and additional examples of agents used in alternative therapeutic regimens, and their methods of use including dosing and administration regimens, will be known to a physician versed in the art. Furthermore, methods of use of chemotherapeutic agents and other agents used in alternative therapeutic regimens in combination therapies, including dosing and administration regimens, will also be known to a person versed in the art.

Prostate Cancer

Androgen action and the functional status of AR are important mediators of prostate cancer progression. High AR expression correlates with lower recurrence-free survival and disease progression (Heinlein and Chang 2004). AR activity is an important mediator of prostate cancer growth and survival. Androgen dependent and independent prostate cancer cells respond differently to upregulation of SEMA3C (Herman and Meadows 2007).

Any terms not directly defined herein shall be understood to have the meanings commonly associated with them as understood within the art of the invention. Certain terms are discussed below, or elsewhere in the specification, to provide additional guidance to the practitioner in describing the compositions, devices, methods and the like of embodiments of the invention, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples in the specification, including examples of terms, is for illustrative purposes only and does not limit the scope and meaning of the embodiments of the invention herein.

Other aspects and features of the present invention will become apparent to those ordinarily skilled in the art upon review of the following description of specific embodiments of the invention in conjunction with the accompanying figures. The invention is herein further described with reference to the following, non-limiting, examples. A description of the experimental procedures employed follows the examples.

SEMA3C in Prostate Cancer

The present disclosure provides significant support for the use of SEMA3C inhibitors for the treatment of prostate cancer. It is shown herein, that higher SEMA3C mRNA and secreted protein levels are associated with androgen sensitive and hormone refractory prostate cancer cells, that SEMA3C is upregulated upon androgen withdrawal from prostate cancer cells, and that SEMA3C has higher expression levels in tissue samples from more progressed prostate cancers. Additionally, it is shown herein, that certain RNA interference compounds directed towards SEMA3C are capable of inhibiting SEMA3C expression, and that such inhibition causes inhibition of cell growth and induction of apoptosis in prostate cancer cells, and that such cell growth inhibition occurs in a SEMA3C dependent manner. Furthermore, it is shown herein that SEMA3C is a growth factor for prostate cancer cells. It is demonstrated herein that treatment of prostate cancer xenograft mice with a SEMA3C antisense oligonucleotides significantly reduced tumour volume and PSA threshold. Peptides are also shown herein to interfere with the interaction of SEMA3C with its cognate protein receptors or other binding partners. Treatment of prostate cancer cells with such peptides reduced prostate cancer cell growth.

Accordingly, the present application provides novel compositions and methods for the treatment of diseases or conditions for which it would be desirable to reduce the expression or activity of SEMA3C (for example, prostate cancer). The prostate cancer may have escaped the prostatic capsule, for instance advanced prostate cancer or may be advanced local prostate cancer. The SEMA3C inhibitor may be an RNA or DNA interference compound. The SEMA3C inhibitor may be an RNA interference compound having a sequence substantially similar to SEQ ID NO: 2. The SEMA3C inhibitor may be a peptide. The SEMA3C inhibitor may be a peptide having an amino acid composition substantially similar to SEQ ID NO: 3, or a fragment thereof. The SEMA3C inhibitor may be an antibody or an intrabody that binds to a peptide having an amino acid composition substantially similar to SEQ ID NO: 1 or 3 or fragments thereof. Alternatively, the SEMA3C inhibitor may be a small molecule, such as Zinc00163599 (2-bromo-N-(2-methoxyphenyl)propanamide).

In another embodiment of the invention, there is provided a polynucleotide composition comprising a nucleic acid sequence substantially similar to SEQ ID NO: 2. In another embodiment of the invention, there is provided a pharmaceutical composition comprising a polynucleotide composition with a nucleic acid composition substantially similar to SEQ ID NO: 2.

EXAMPLES

The following working examples are provided for illustrative purposes, and are not intended to be limiting, as such.

Example 1

SEMA3C is Up-regulated Upon CRPC Progression

The present inventors have examined SEMA3C mRNA levels and secreted protein levels in benign prostatic hyperplasia BPH-1 cells, androgen sensitive LNCaP cells, C4-2 cells which is a lineage derived castration resistant subline of LNCaP and androgen independent DU145 cells and found that androgen independent DU145 and hormone refractory C4-2 cells indeed expressed 6- to 8-fold higher levels of SEMA3C than androgen sensitive LNCaP and non-malignant BPH-1 cells (FIG. 1) supporting the notion that increased SEMA3C expression is associated with progression to CRPC.

Example 2

SEMA3C is Up-regulated Upon Stress-induction by Androgen Withdrawal

Figure 2:
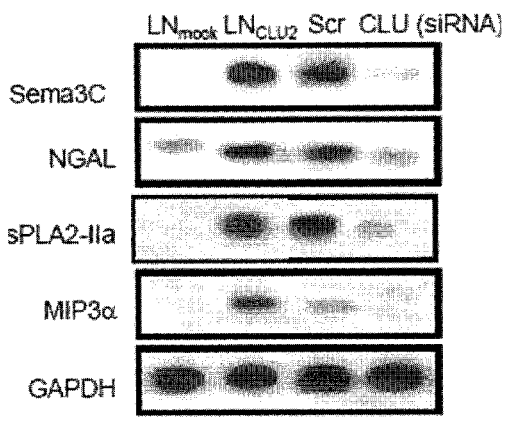
FIG. 2. A shows a Gene-tree analysis, where CLU modulates NF-kB dependent genes, and where genes are grouped based on whether there was a gain or loss of sCLU-2 function. The gene list was created by comparing genes upregulated 2 fold when sCLU-2 was overexpressed (LNmock parental vs LNCLU2, n=2 biological replicates) to genes downregulated 2 fold when sCLU-2 was knocked down) (Scr vs siRNA, n=2). Data from Imagene were analyzed in GeneSpring 6.1 (Silicon Genetics, Redwood City, Calif.) using a per spot and per chip intensity dependent (Lowess) normalization for profiling significant changes in gene expression. Two types of analyses were performed in GeneSpring:supervised (background correction, Lowess normalization, confidence t-test, Benjamini Hochberg multiple comparison test, and fold change); and unsupervised (background correction, per spot normalization, gene-tree hierarchical clustering using standard correlation). B shows a Northern blot validation of gene expression changes.
Figure 2:
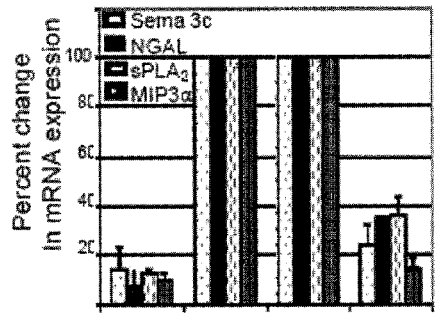
Figure 3:
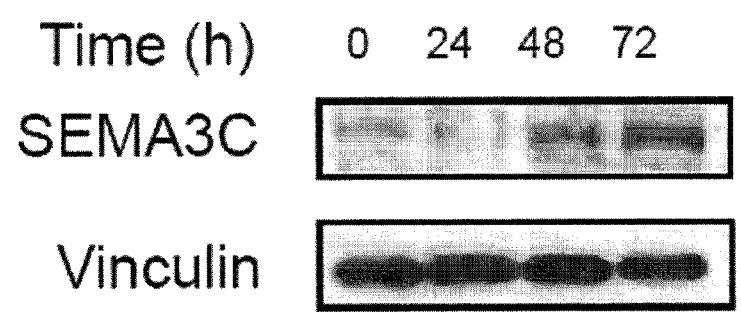
FIG. 3. shows an increase of SEMA3C on Western blot after androgen deprivation in LNCaP cells that were cultured in 5% CSS media and harvested at 24 hours intervals each up to 72 hours. Expression of SEMA3C was determined by immunoblotting with a Vinculin control.

As mentioned above, we identified SEMA3C as a clusterin regulated gene that is upregulated in a NFkB dependent manner in LNCaP cells (FIG. 2). To examine whether SEMA3C is induced following androgen withdrawal, we assessed secreted SEMA3C protein levels in LNCaP cells cultured under androgen depleted conditions. As shown in FIG. 3, the levels of SEMA3C secreted by LNCaP cells increased in a time dependent manner when cultured in androgen depleted 10% charcoal stripped serum (CSS).

Example 3

High Sema3C Expression is Associated with Progression to CRPC

Figure 4:
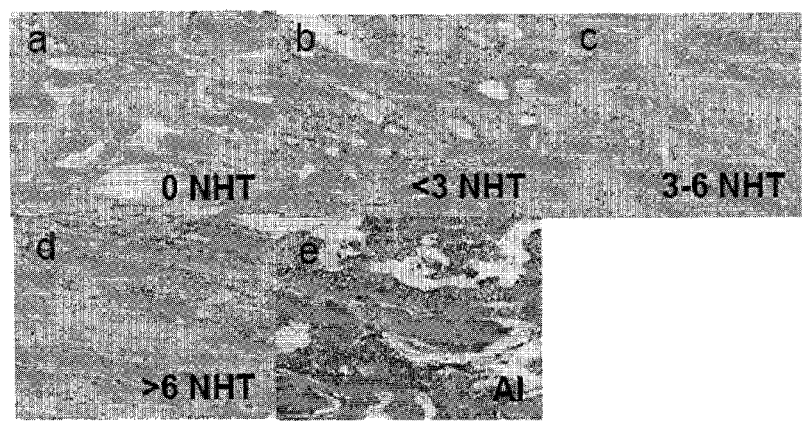
FIG. 4. A shows a representative microscopic fields of SEMA3C immunostaining in a human prostate cancer tissue microarray. In most tumor cells of micrograph a-c, immunoreactivity is very weak, but micrograph d shows prostatic cancer after 6 months of neoadjuvant hormonal therapy (NHT) with more intense immunoreactivity of cancerous glands and micrograph e shows highly intensive and uniformly reactive androgen-independent tumors. B shows a bargraph of mean Semaphorin 3C staining after androgen ablation. Specimens were graded from 0 to 3 intensity representing the range from no staining to heavy staining by visual scoring and automated quantitative image analysis by proplusimage software. Data from 232 samples were used to calculate average±SD. All comparisons of stain intensity were made at ×200 magnification. The asterisks indicate significances between groups (*, $P<0.05$).
Figure 4:
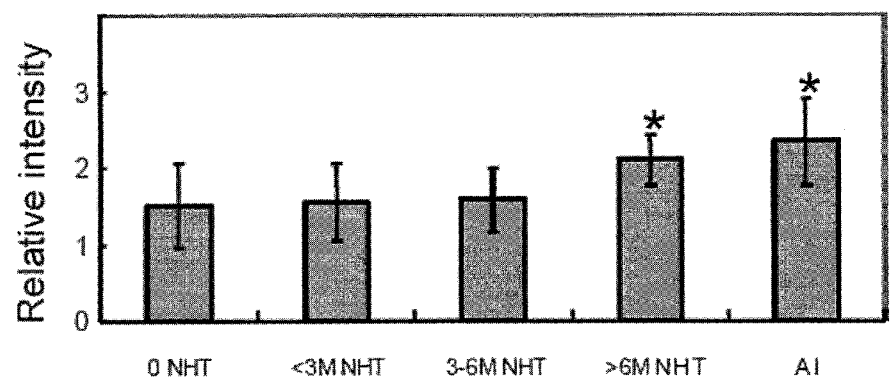

Next, to determine whether SEMA3C is also upregulated following androgen ablation in clinical samples, immunostaining was performed on a neo-adjuvant hormone therapy (NHT) tissue microarray representing 232 human CaP specimens from hormone naïve, post-hormone treated cancers grouped into <3 months, 3-6 months, >6 months and CRPC. As shown in FIG. 4, SEMA3C was significantly upregulated in CaP specimens collected from men after >6 months of NHT and in CRPC specimens, confirming that high SEMA3C is associated with CRPC progression.

Example 4

Generation and Characterization of SEMA3C Targeted ASO

Figure 5:
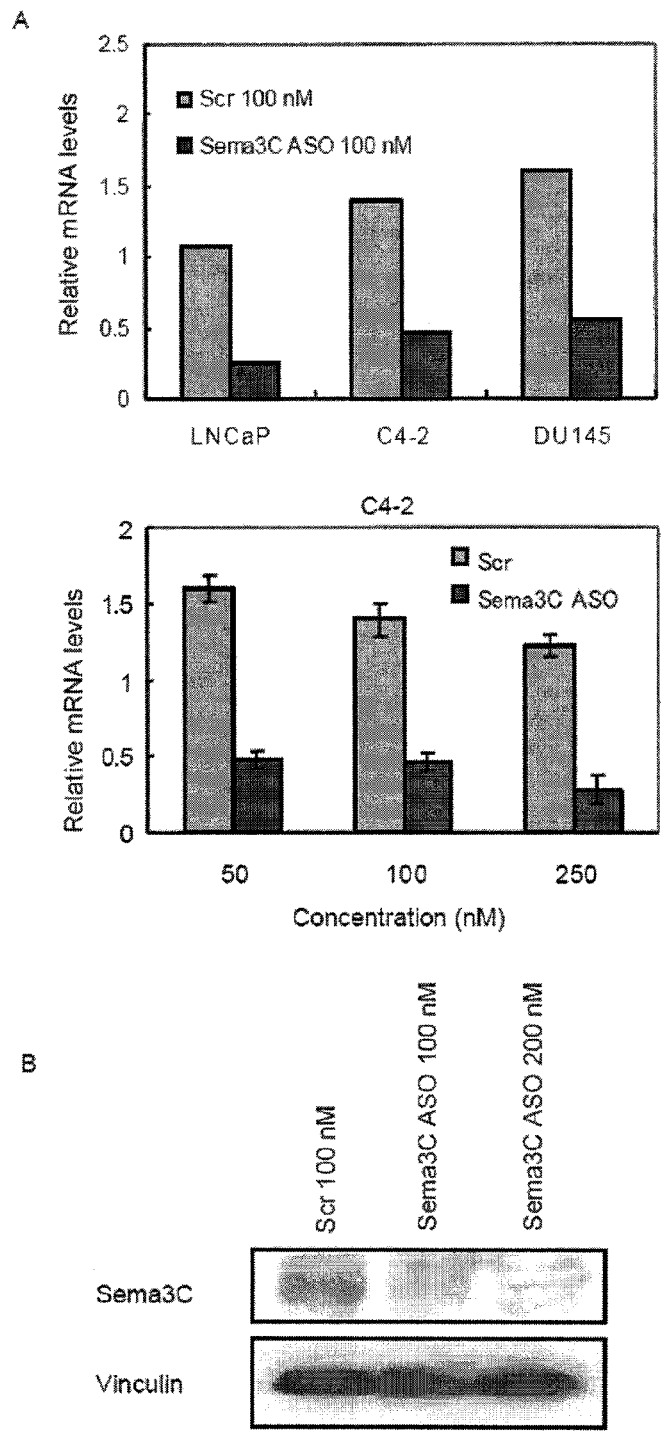
FIG. 5. shows antisense oligonucleotide (ASO) treatment down-regulates SEMA3C expression. A shows cells that were treated daily with indicated concentrations of SEMA3C ASO or scrambled ASO (Scr) controls for 2 days. Total RNA was extracted from culture cells 24 hours after transfection and the knockdown effect by SEMA3C ASO was analyzed by quantitative-PCR. mRNA levels are shown for cells treated with oligofectamine only was considered as 1 in each cell lines. B shows C4-2 cells Semaphorin 3C secretion, 48 hours after transfection by ASO as compared to scrambled ASO (Scr) as assessed by Western blotting, with a Vinculin control.

To characterize the functional role of SEMA3C, we designed an ASO against nucleotide positions 1-20 of the SEMA3C coding sequence (SEQ ID NO: 2). From quantitative real-time polymerase chain reaction (qPCR) analyses, we found that this SEMA3C targeted ASO effectively inhibits SEMA3C expression in LNCaP, C4-2 and DU145 cells (FIG. 5). In addition, SEMA3C mRNA and secreted protein was inhibited in an ASO-dose dependent manner in C4-2 cells (FIG. 5).

Example 5

Figure 6:
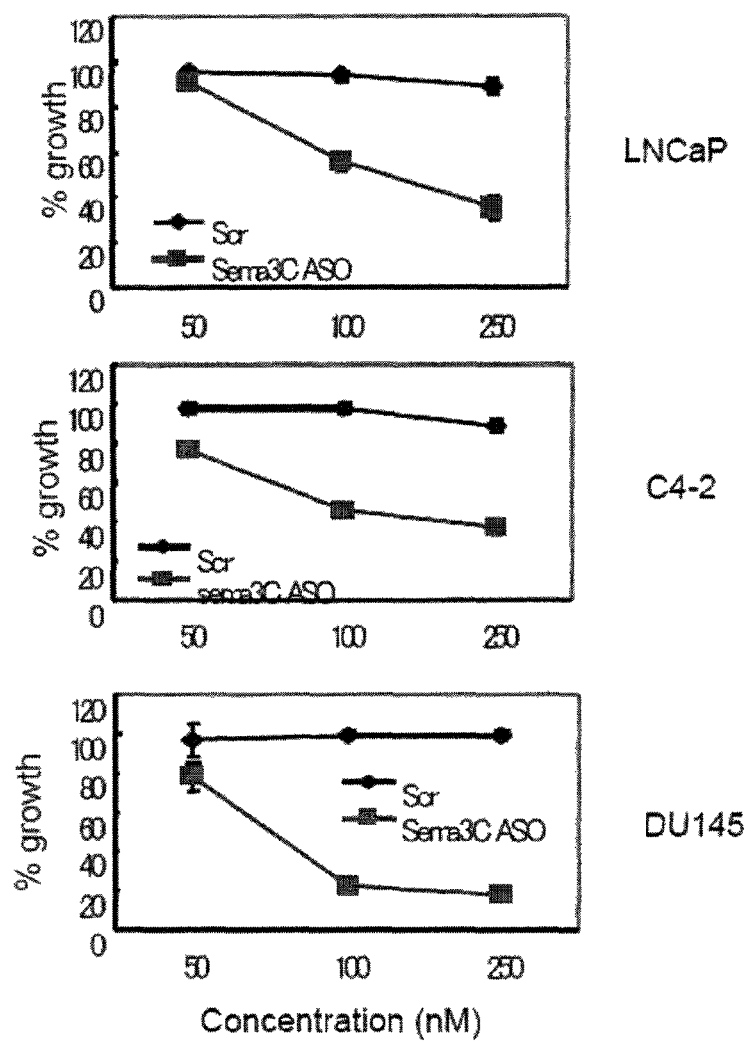
FIG. 6. shows line plots of % cell growth in LNCaP, C4-2 and DU145 cells following SEMA3C ASO and Scr treatment at various concentrations (dose dependent).
Figure 7:
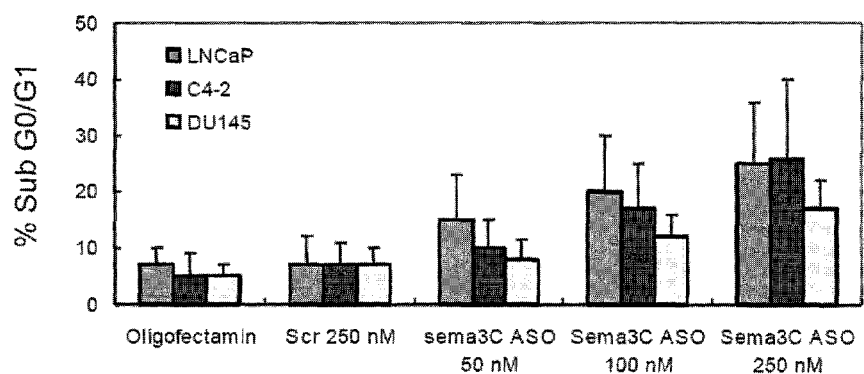
FIG. 7. shows that Semaphorin 3C silencing induces apoptosis. A shows a plot for the % of cells that are sub G0/G1 for LNCaP, C4-2 and DU145 cells treated with different concentrations (50 nM, 100 nM, and 250 nM) of SEMA3C ASO as compared to 250 nM of Scr and oligofectamin at 48 hours after transfection, as analyzed by flowcytometry. B shows a Western blot of DU145 cells that were treated at various concentration of ASO as compared to Scr and oligofectamin at forty-eight hours after transfection, when cell lysates from treated cells were analyzed for Caspase-3, -8, -9, cleaved PARP and GAPDH using specific antibodies.
Figure 7:
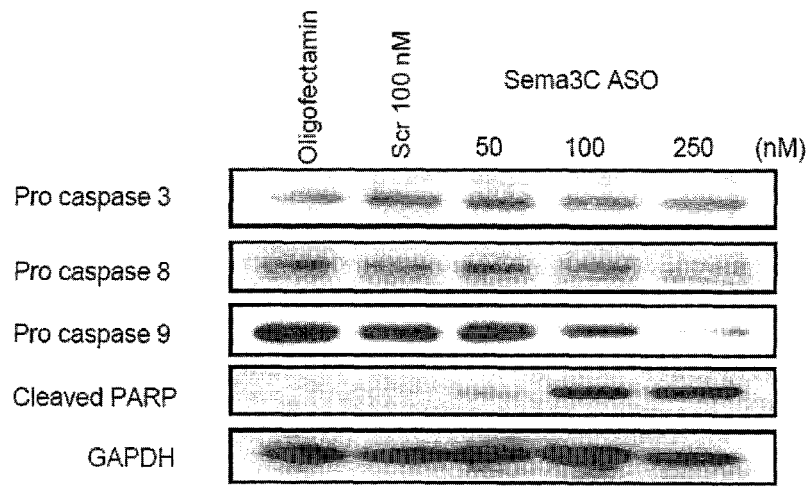

SEMA3C ASO Inhibits Cell Growth and Induces Apoptosis of Cap Cells in a Sequence Specific Manner ASO treatment inhibited growth (FIG. 6) and induced apoptosis as monitored by sub G0/G1 DNA content analyses (FIG. 7A) of LNCaP C4-2 and DU145 cells in a dose dependent manner. SEMA3C ASO-induced apoptosis was associated with an increase in PARP cleavage and a decrease in levels of pro-caspase 3 and pro-caspase 8 and pro-caspase 9 in DU145 cells (FIG. 7B).

Example 6

SEMA3C ASO inhibits CaP cell growth in a SEMA3C Dependent Manner

Figure 8:
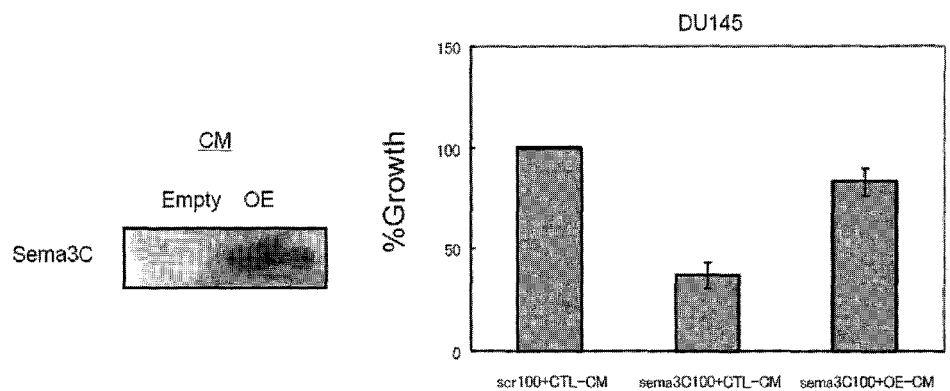
FIG. 8. shows that recombinant SEMA3C is able to rescue inhibition of cell growth induced by SEMA3C ASO. On the left an SEMA3C immunoblot of conditioned media derived from LNCaP cells transduced with empty vector (CTL) or SEMA3C expressing lentivirus (OE) is shown. On the right, a bar plot shows that the inhibition of cell growth induced by ASO treatment is reversed by addition of conditioned media with SEMA3C (CM) but not with conditioned media lacking SEMA3C.

The issue of target specificity and off-target effects is an important consideration in the use of ASO in functional genomics. The best and most robust way to control for ASO specificity is to rescue the phenotype induced by the ASO via genetic or protein reconstitution of the target. To this end, LNCaP cells were transduced with a lentivirus expressing SEMA3C or empty vector as control and conditioned media was prepared. Conditioned media from cells expressing SEMA3C (SEMA3C CM) but not conditioned media from empty vector transduced cells (Mock CM) was able to rescue inhibition of cell growth of DU145 cells induced by ASO treatment confirming the target specificity of SEMA3C ASO (FIG. 8).

Example 7

SEMA3C is a Growth Factor for CaP Cells

Figure 9:
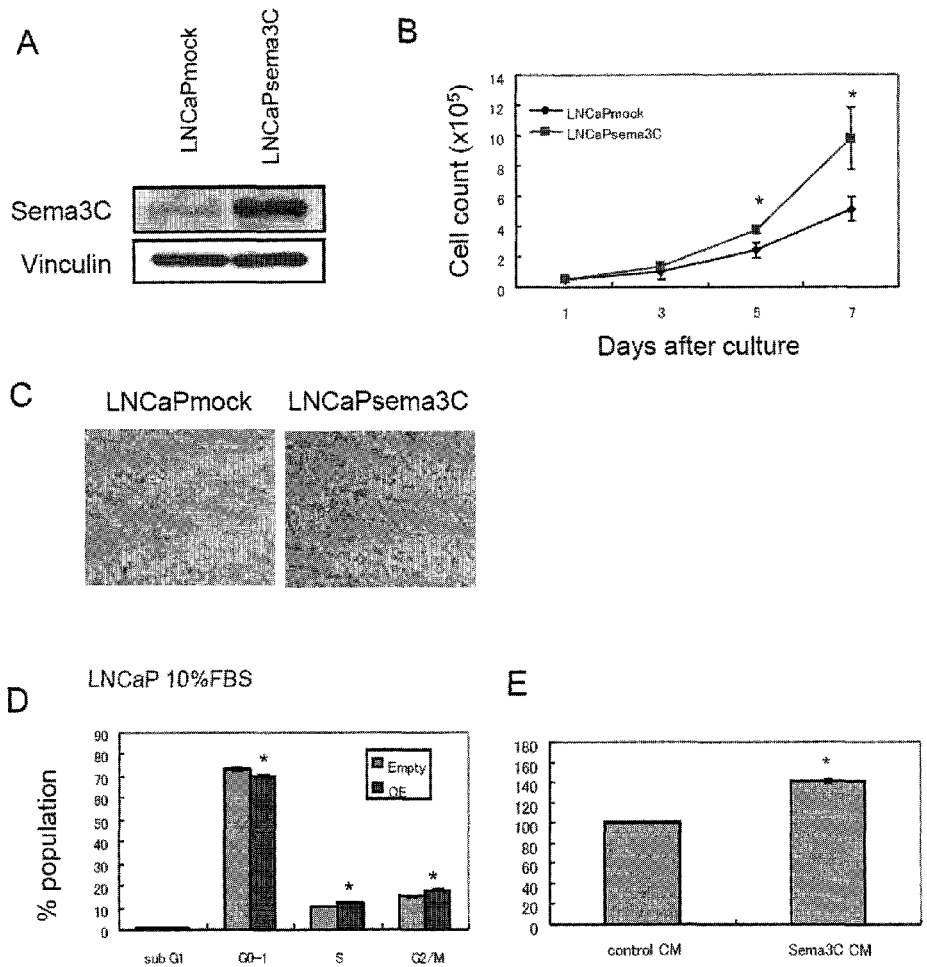
FIG. 9. shows that semaphorin 3C increases cell growth in LNCaP cells. A shows a Western blot confirming that full-length cDNA for human Semaphorin 3C was subcloned into the lentiviral vector pFUGWBW as compared to the mock control (with Vinculin positive control). Five days after blasticidin treatment, cells were cultured for 48 hours in 10% FBS media and protein was extracted from cultured cells 6 hours after BFA treatment and Semaphorin 3C and vinculine protein levels were analyzed by Western blotting. B shows a plot of cell count for SEMA3C overexpressing LNCaP (LNCaP-sema3C) and empty vector transduced cells (LNCaP mock) cultured in 10% FBS media, where the cell count was performed at 2 day intervals each up to day 7 (*asterisks indicate significances between groups (*, P<0.05)). C shows photomicrographs of each cell type taken at day 7. D shows a bar plot of a cell cycle analyses performed by flow cytometry of bromodeoxyuridine incorporation and propidium iodide staining of LNCaP-Sema3C and LNCaP mock cells, where the statistical significance is indicated by asterisks (*; P<0.05). E shows a bar plot of % cell growth twenty-four hours after culture in 10% FBS media, DU145 cells were cultured each in conditioned media (CM) from LNCaP-empty (control CM) or -Semaphorin 3C (Sema3C CM) for 3 days. Each CM was made from the culture media of each cells cultured in serum-free media for 3 days.

To determine whether SEMA3C is a bona fide growth stimulatory factor, DU145 cells were treated with SEMA3C CM versus Mock CM and cell growth was monitored by direct cell counting of viable cells (FIG. 9E). Consistent with this notion, over-expression of SEMA3C accelerated LNCaP cell growth which correlated with increase proportion of cells in S phase (FIG. 9).

Example 8

SEMA3C ASO Treatment Prevents LNCaP Progression after Castration In Vivo

Figure 10:
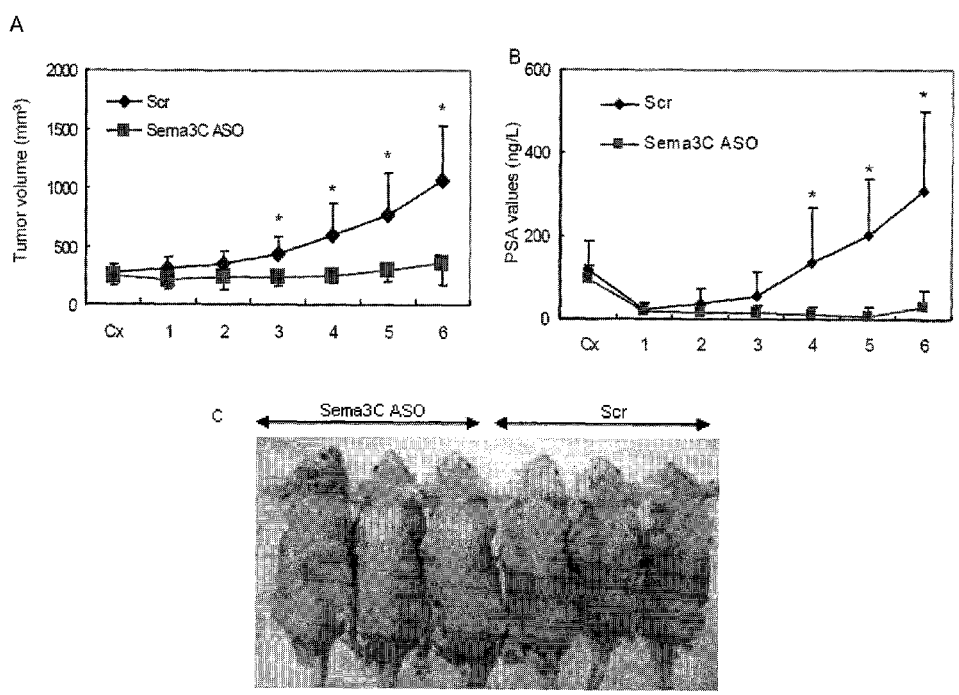
FIG. 10. shows the effect of Semaphorin 3C ASO treatment on LNCaP tumor growth in vivo. A and B show tumor volume and PSa values, respectively, for mice bearing LNCaP tumors randomly selected for treatment with Semaphorin 3C ASO (SEMA3C ASO) or scrambled ASO (Scr). The mice were castrated at a PSA threshold of 75 ng/L and tumor volume and serum PSA were monitored weekly. Semaphorin 3C ASO or scrambled ASO were injected i.p. (12.5 mg/kg/mouse) at 2 day intervals for 6 weeks and tumor volume was calculated by the formula: length×width×depth×0.5236. Points, mean tumor volume in each experimental group containing 10 mice; bars, SD. * differ from scrambled control (P<0.05) by Student's t test. C shows pictures of representative mice following treatment with SEMA3C ASO and Scr.

Twenty male athymic nude mice bearing LNCaP xenograft tumors were castrated at a PSA threshold of 75 ng/ml and were randomly selected for treatment with SEMA3C ASO versus scrambled control. Mean tumor volume and PSA were similar in both groups at the beginning of the treatment. Beginning 1 Day after castration, 12.5 mg/kg of ASO was administered every other day by intraperitoneal (i.p.) injection for 6 weeks and tumor volume and serum PSA levels were monitored once weekly. As shown in FIG. 10, following castration, LNCaP tumor volume and serum PSA levels decreased and remained low throughout the time course of the experiment in mice treated with SEMA3C ASO, compared with those treated with scrambled controls which exhibited gradual progression to CRPC. All mice treated with castration plus SEMA3C ASO had a significant inhibition of CRPC tumor growth during the 6 weeks of analyses. No side effects were observed with SEMA3C ASO or scrambled control treatment.

Example 9

SEMA3C Truncated Peptide is a Potent Inhibitor of LNCaP Cell Growth

Figure 11:
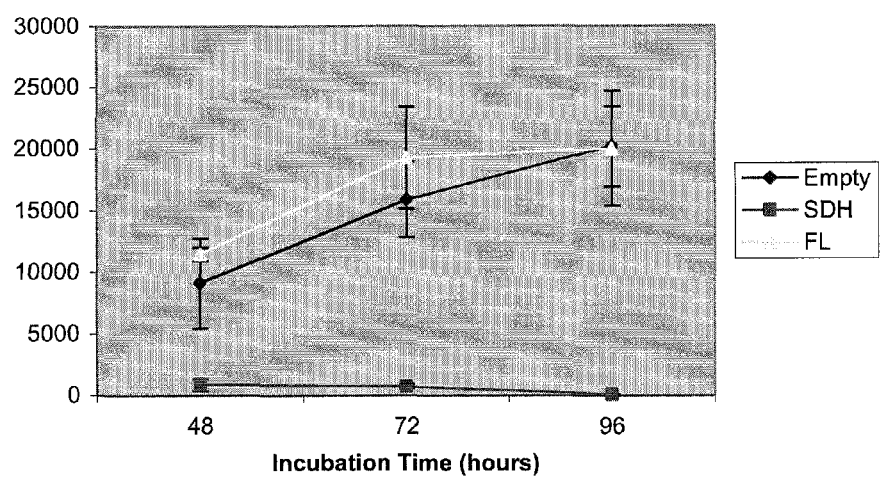
FIG. 11. shows that a truncated SEMA domain containing SEMA3C mutant acts as a potent inhibitor of LNCaP cell growth in a line plot of proliferation of LNCaP cells cultured in the presence of conditioned media from stable lentivirally transduced HEK-293T cells expressing full-length Sema3C (FL—SEQ ID NO: 1), Sema Domain (SDH—position 1-495 of full length SEMA3C, SEQ ID NO: 3) or empty vector over time as monitored by 3H-thymidine incorporation.

LNCaP cells were cultured in the presence of conditioned media from stable lentivirally transduced HEK-293T cells expressing full-length SEMA3C (FL), truncated SEMA3C (SDH) or empty vector and LNCaP cell proliferation was monitored by 3H-thymidine incorporation. LNCaP cells cultured in the presence of truncated SEMA3C(SDH) displayed significantly lower growth than those cells grown in the presence of full length SEMA3C (FL) or no SEMA3C (empty vector) (FIG. 11). The truncated SEMA3C used in this experiment comprised a SEMA domain from SEMA3C, and corresponded to SEQ ID NO: 3.

Example 10

Full Length SEMA3C and Truncated SEMA3C Influence LNCaP Cell Plating Efficiency

Figure 12:
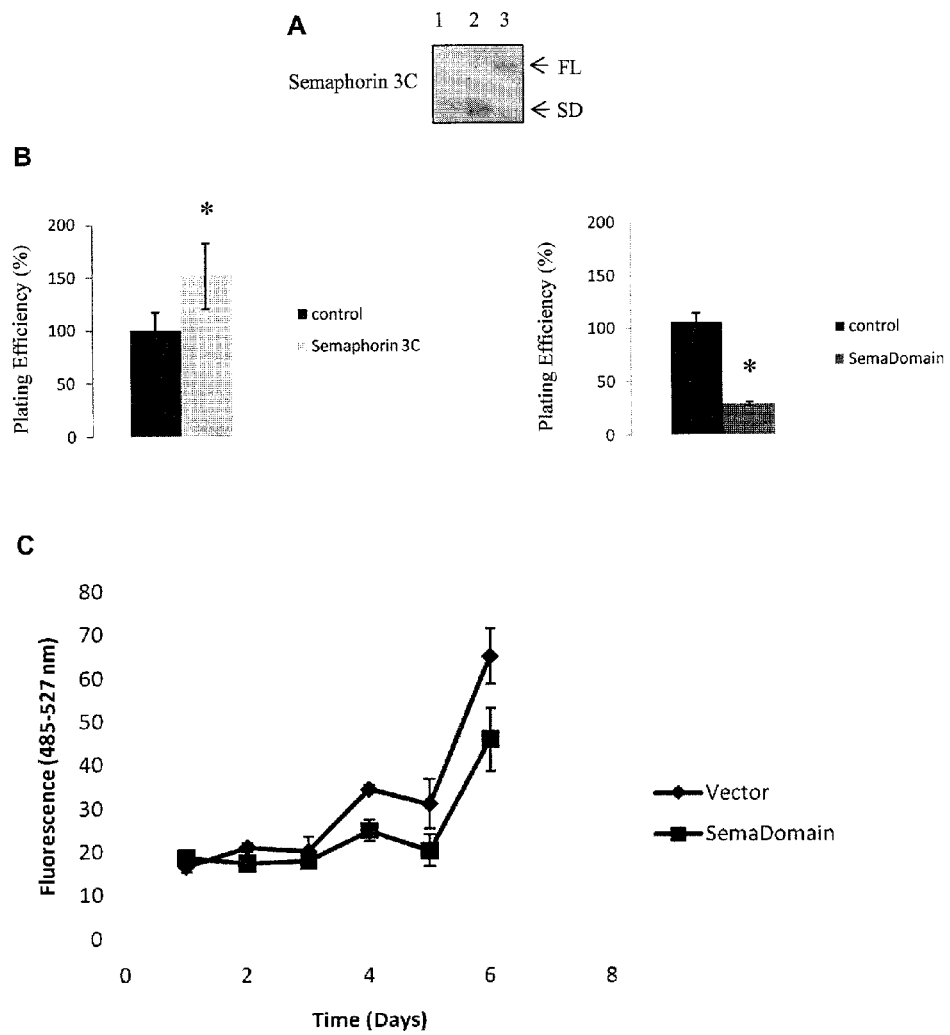
FIG. 12 shows Semaphorin 3C enhances the plating efficiency of LNCaP cells in soft agar. A shows a Western blot of Semaphorin 3C expression in LNCaP cells, for lentiviral expressed vector alone (lane 1), Semaphorin 3C, full-length (lane 3, FL), and Sema Domain (lane 2, SD) detected using Sema3C(N20) antibody (from Santa Cruz biotechnology Inc). B shows bar graphs % plating efficiency of LNCaP cells (5000) plated in 0.7% agarose containing 4% FBS, where colonies were counted four weeks after plating. The bars represent the Mean and SEM (n>5) plating efficiency (%) LNCaP cells expressing stable full length (left panel) or the SemaDomain (right panel) of Semaphorin 3C relative to LNCaP cells expressing vector alone (control). Data is representative of typical results observed in greater than three independent experiments (*P<0.01). C shows a line plot representing LNCaP cell proliferation over a 6 day time course, with LNCaP cells (500/well) expressing either vector alone or the SEMA3C Semadomain. The LNCaP cells were seeded in 48-well plates in RPMI medium containing 1% serum and cell growth (fluorescence) was monitored using the CyQuant Cell Proliferation assay kit (Invitrogen, Mississauga), where the data points represent the Mean and SEM fluorescence of replicates (n=4).

The over-expression of full length semaphorin 3C enhances plating efficiency and growth of LNCaP cells in soft agar in contrast to the expression of the sema domain alone, which suppresses colony formation in soft agar (FIG. 12). Soft agar growth is used to measure cell anchorage-independent proliferation potential and is one of the most important and most commonly used assays to detect cell transformation and in this case demonstrates that the sema domain can act as an inhibitor of anchorage independent cell proliferation.

Example 11

Figure 13:
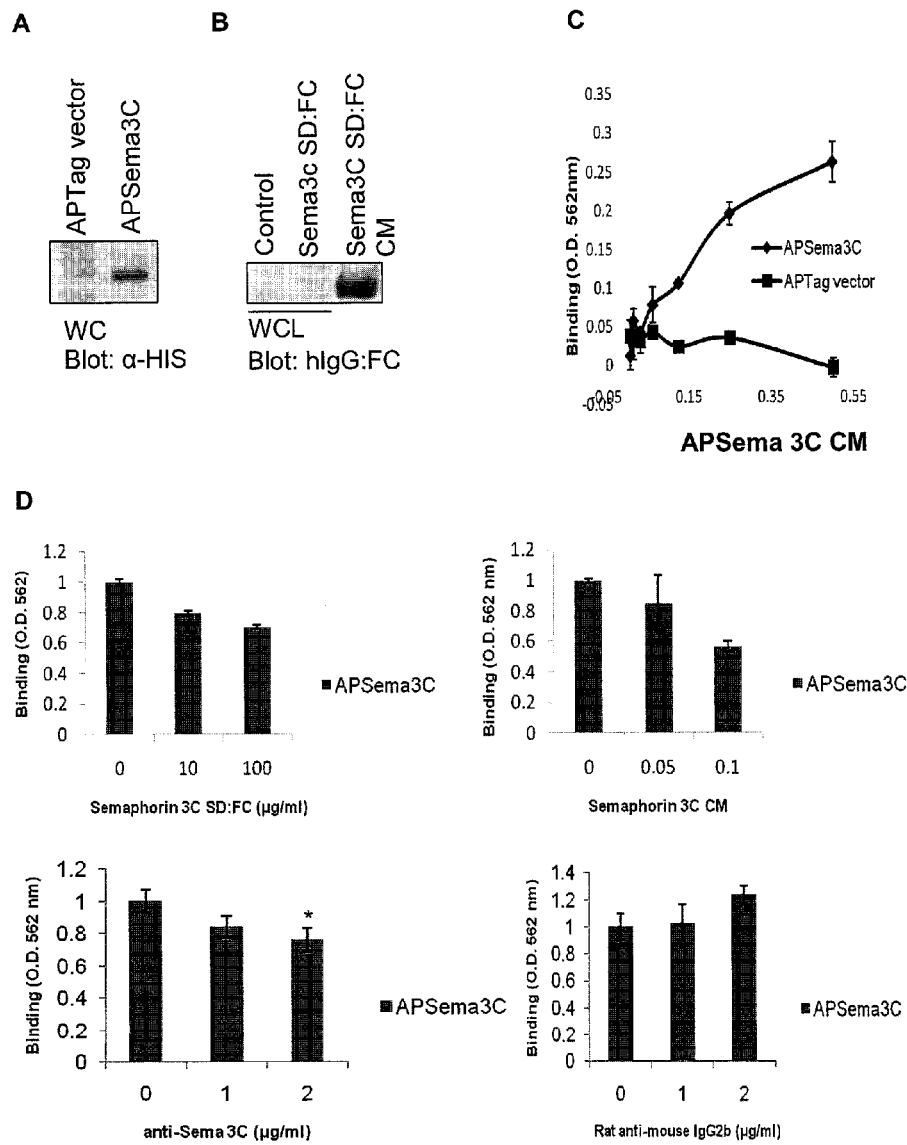
FIG. 13 shows that Semaphorin 3C:alkaline phosphatase fusion protein (APSema3C) has specific binding to DU145 cells. A shows a Western Blot of APSema3C expressed in 293T cells detected using THE™ anti-His monoclonal antibody (GeneScript Corp. NJ.). B shows a Western Blot of the expression of Semaphorin 3C Sema domain:Fc fusion protein in 293T cells using an anti-human IgG Fc region antibody (R&D systems, MN). C is a line plot that shows binding of APSEMA3C and AP alone on DU145 cells as measured by alkaline phosphatase activity. D shows 4 bar graphs of competitive cell surface receptor binding using an alkaline phosphatase activity assay, where this binding can be competed off by adding either Sema domain:Fc Fusion protein (top left), full-length Semaphorin 3C protein (top right), or monoclonal anti mouse-Semaphorin 3C (bottom left) (R&D Diagnostics, MN), but not by Rat ant-mouse IgG2b (bottom right) (Sigma).

Competitive Binding of SEMA3C Alkaline Phosphatase Fusion Protein Shows Displacement by Full-ength Sema3C, Sema Domain and a Mouse Anti-Sema3C Monoclonal Antibody in DU 145 Cells Semaphorin 3C was fused in-frame with the human placental secreted alkaline phosphatase, and the resulting AP fusion protein called APSema3C was then used to monitor cell surface receptor binding by an alkaline phosphatase activity assay (FIG. 13). The specific binding of APSema3C fusion protein on to DU145 cells can be competed off by adding either Sema domain: Fc fusion protein, full-length Sema3C or a mouse anti-Sema3C monoclonal antibody, but is not competed off by Rat anti-mouse IgG2b (control).
Generation of Full-length Semaphorin 3C Alkaline Phosphatase Fusion Protein.

Full length Semaphorin 3C including its native signal peptide was amplified by PCR using Semaphorin3C cDNA NM_006379 (Origene cDNA clone SC116160, Origene, Rockville, Md.) as a template for PCR. Semaphorin 3C-specific 5'- and 3'-primers containing NheI and BglII restriction sites were used for PCR amplification. The resultant PCR product was cloned in-frame to the Alkaline Phosphatase coding sequence by ligation into the NheI/BglII sites of pAPtag-5 vector (GenHunter Corporation, Nashville, Tenn.). The final construct was confirmed by DNA sequence analysis. Expression of the Semaphorin 3C AP fusion protein was confirmed by Western blot from whole cell lysates and conditioned medium using anti-Semaphorin 3C(N-20) antibody or THE™ anti-His monoclonal antibody (Genescript Corp. N.J.).
Alkaline Phosphatase:Semaphorin 3C Fusion Protein Shows Specific Binding to DU145 Cells.

A binding assay was developed in DU145 cells essentially as previously described by Flanagan et al. 1990. The day before the binding assay, DU145 cells (20,000/well) were seeded in growth medium (DMEM containing 10% FBS) on 96-well tissue culture plates. Conditioned medium was harvested from Semaphorin 3C-AP expressing 293Tcells 48 hours after reaching subconfluence. The conditioned medium was serially diluted two-fold in binding buffer HBHA (20 mM HEPES, 150 mM NaCl, 0.1% azide, 5 g/L BSA, 5 mM $CaCl_2$, 1 mM $MgCl_2$). Growth medium was then removed and the cells were washed once with HBHA buffer and replaced with the serially-diluted Semaphorin-AP CM. The cells were incubated for 90 minutes at RT. Plates were washed with HBHA seven times over a period of 10 minutes. Cells were fixed with (60% acetone, 3% formaldehyde) for 30 minutes on ice. Cellular alkaline phosphatase was inactivated by floating the plates on a 65° C. water bath for 20 minutes. Cells were then washed a further three times with HBHA prior to detection of AP activity using NBT/BCIP made up in AP buffer (100 mM Tris pH 9.5, 100 mM NaCl, 5 mM $MgCl_2$). Plates were incubated in the dark overnight and then read at optical density (550-562 nm) in a plate reader.

Generation of Semaphorin 3C Semadomain Fusion protein. The Semadomain containing its native signal peptide (amino acids (1-495) of Semaphorin 3C (NM_006379, Origene clone SC116160, Origene, Rockville, Md.)) was amplified by PCR using Semaphorin 3C-specific 5' and 3' primers containing Age1 and BglII restriction sites for cloning. The Semadomain was therefore fused in-frame to human IgG1 engineered Fc by restriction site specific DNA ligation into pFUSE-hIgG1e1-Fc1 (Invivogen, San Diego, Calif.). The final cDNA construct was confirmed by DNA sequencing. The final fusion construct was then transfected into HEK 293T cells and stable expressing clones were selected by antibiotic selection in zeocin (10 µg/ml) (Invitrogen, Missisauga, On). Expression of the Semadomain:Fc (SD:FC) fusion protein was detected by Western Blot using anti-hIgG: 96-well plates. Conditioned medium from approximately 1,000 clones was screened by indirect-ELISA using monoclonal anti-human IgG1Fc-specific antibodies (clone GG7, 5 µg/ml) as capture, (Sigma, St. Louis, Mo.) and goat anti-Human IgG (Fc-specific)-peroxidase (1:30,000, Sigma, St. Louis, Mo.) as secondary antibody. Detection was carried out using Tetramethyl benzidine (TMB). Plates were incubated in the dark for 60 minutes and then read on a plate reader at 450 nm. A clone secreting a high level of Semadomain:Fc fusion protein was identified and used for all subsequent experiments. The Semadomain:Fc fusion protein was further purified from conditioned medium by Protein A/G affinity chromatography and then concentrated 70-fold on Amicon Ultra centrifugal filters 10,000 MWCO.

Example 12

Figure 14:
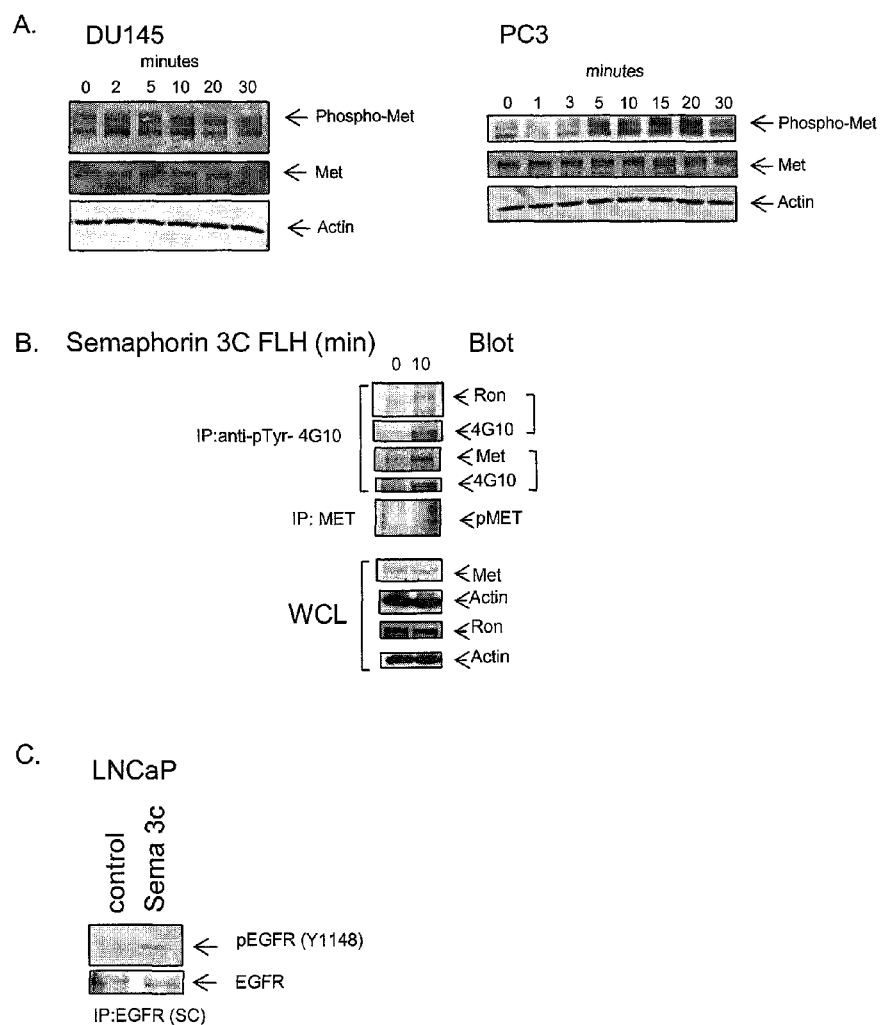
FIG. 14 shows that Semaphorin 3C signals through protein tyrosine kinase receptors MET and RON in DU145 and PC3 cells and through EGFR in LNCaP cells. A shows time course of Semaphorin 3C stimulated DU145 and PC3 cells on Western Blots of MET phosphorylation in WCL (20 µg) as detected with phospho-Met antibodies (Cell signaling) blots were reprobed with total MET and actin as loading control. B shows WCL (1.0 mg) from Semaphorin 3C stimulated (10 min) or mock-treated DU145 cells were immunoprecipitated with anti phospho-tyrosine (clone 4G10) or MET and the Western Blots were probed with either MET, RON (Sanata Cruz), or anti-phosphotyrosine (4G10, Millipore) and phospho-MET (Cell signaling). C shows WCL (1.0 mg) was immunoprecipitated from control or Semaphorin 3C-treated (10 min) LNCaP cells on Western Blot showing EGFR phosphorylation using anti-phospho-EGFR (tyrosine 1148, Cell signaling). The blot was reprobed with total EGFR antibodies (Santa Cruz) to demonstrate that equal amounts of EGFR were immunoprecipitated.
Figure 15:
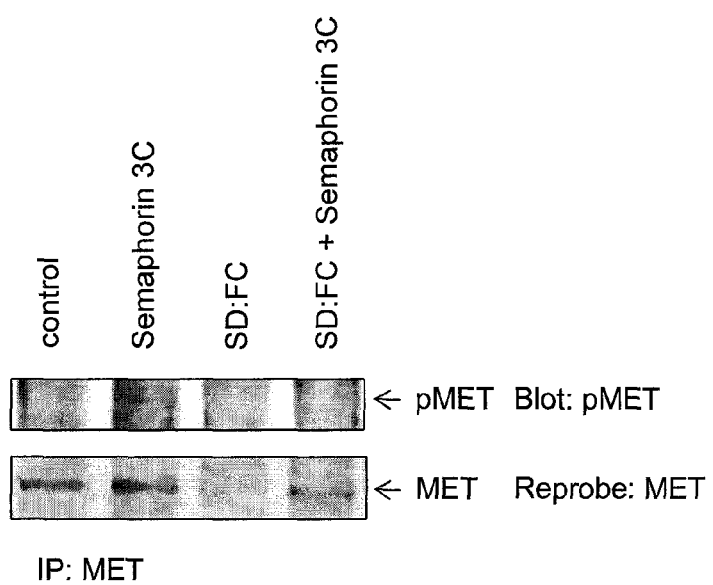
FIG. 15 shows Western blots where Semaphorin 3C-mediated tyrosine phosphorylation of MET is inhibited by Sema-domain:Fc fusion protein. DU145 cells were serum starved for 48 hours and, the cells were then preincubated for 1 hour in either medium alone or in the presence of Semadomain:Fc (100 µg/ml) and cells were then mock-treated or stimulated with Semaphorin 3C (1:10) for 10 min at 37° C., 5% CO2. Cell lysates (1000 µg) were immunoprecipitated with anti-MET and analysed by Western Blot using anti-pMET and the blot was reprobed with anti-MET for loading control.

SEMA3C Signals Through Protein Tyrosine Kinase Receptors Met and RON in DU145 and PC3 Cells and Through EGFR in LNCaP Cells The treatment of cells with SEMA3C leads to activation of MET and RON tyrosine kinase receptors in DU145 and PC3 cells, and SEMA3C treatment of LNCaP cells leads to activation of the EGFR (FIG. 14). Semaphorins bind and activate plexin receptors, and plexins have been shown to interact with MET and EGFR via its extracellular domain. Furthermore, the treatment of cells with the SD:Fc fusion protein can block SEMA3C induced phosphorylation of MET (FIG. 15).

Full-length His-tagged Semaphorin 3C was purified using standard nickel column affinity chromatography. The resultant purified Semaphorin3C protein was further concentrated and reconstituted to the original volume with PBS.

Time course of Semaphorin 3C stimulated DU145 and PC3 cells. Equivalent cell densities of either DU145 or PC3 cells were seeded in 6-well plates 24 hour prior to stimulation with Semaphorin 3C. For stimulations the cells were first washed with PBS and reconstituted with or without Semaphorin 3C CM diluted 1:10 in PBS containing 20 mM HEPES. Cells were stimulated in a time course over 30 minutes. At the indicated time point the cells were washed with ice-cold PBS and immediately lysed with RIPA buffer containing complete protease inhibitors supplemented withlmM Na vanadate and 1 mM Na molybdate. The lysed cells were harvested from the plates by scraping and transferred to microtubes. Whole cell lysates (WCL) were centrifuged to remove cellular debris. Proteins from WCL (20 µg) were separated by 8% SDS-PAGE and further analysed by Western Blot for changes in phosphorylation of MET oncoprotein.

Immunoprecipitation

An equivalent density of DU145 or LNCaP cells were seeded in growth medium on 10 cm tissue culture plates. Twenty-four hours later the medium was then replaced with serum-free medium for 60 hours prior to stimulation. Cells were mock-treated or stimulated with 1:10 diluted Semaphorin 3C in PBS containing 20 mM HEPES at 37° C. in 5% $CO_2$. After 10 minutes cells were then lysed in RIPA buffer supplemented with 1 mM Na vanadate and 1 mM Na molybdate. Cell lystaes were harvested from plates by scraping and centrifuged to remove cell debris. The whole cell lysate was then precleared with 30 µL protein A agarose beads for 30 min. A cell lysate (1000 µg) in a volume of 500 µL was immunoprecipitated with 1.0 µg/ml, anti-phosphotyrosine (clone 4G10, Upstate, Temecula Calif.), anti-MET (C-28) or anti-RON (Santa Cruz, LaJolla Calif.) for DU145 cells. LNCaP cells were similarly immunoprecipitated with anti-EGFR antibody (528, 2.0 µg/ml), (Santa Cruz Biotechnology, Inc., LaJolla Calif.). Cell lysates were exposed to the immunoprecipitating antibodies overnight at 4° C. Immune complexes were then incubated for 2 hours at 4° C. with the appropriate protein A/G agarose beads. The immunoprecipitations were centrifuged and washed 3 times with PBS and the final bead pellet was reconstituted in 30 µL sample buffer boiled for 5 minutes and the samples were separated by 8% SDS-PAGE followed by Western Blot. Western Blots were probed with the following antibodies as suggested by the manufacturers: anti-phosphoMET (Y1234/1235), anti-MET, anti-pEGFR (tyr 1148), (Cell signaling, Pickering, ON), anti-Ronβ (C-20), anti EGFR (528), (Santa Cruz Biotechnology, Inc, LaJolla Calif.), Anti-phosphotyrosine (clone 4G10, Upstate, Temecula Calif.).

DU145 cells were seeded on 10 cm dishes in Growth medium (DMEM containing 10% FBS). Once the cultures reached 70% confluence the medium was replaced with DMEM in the absence of serum and incubated for an additional 48 hours. Cells were then preincubated for 1 hour in either medium alone or in the presence of Semadomain:Fc fusion protein (100 µg/ml). Cells were then mock-treated or stimulated with Semaphorin 3C (1:10) for 10 min at 37° C., 5% $CO_2$. Cells were immediately washed once in ice-cold PBS, followed by lysis with RIPA buffer containing protease inhibitors, the protein lysates were harvested by scraping and the cell debris and membranes were removed by centrifugation. Whole cell lysates (1000 µg) were immunoprecipitated as described above with anti-MET and analysed by Western Blot using anti-pMET. The blot was stripped and reprobed with anti-MET as loading control.

Example 13

Figure 16:
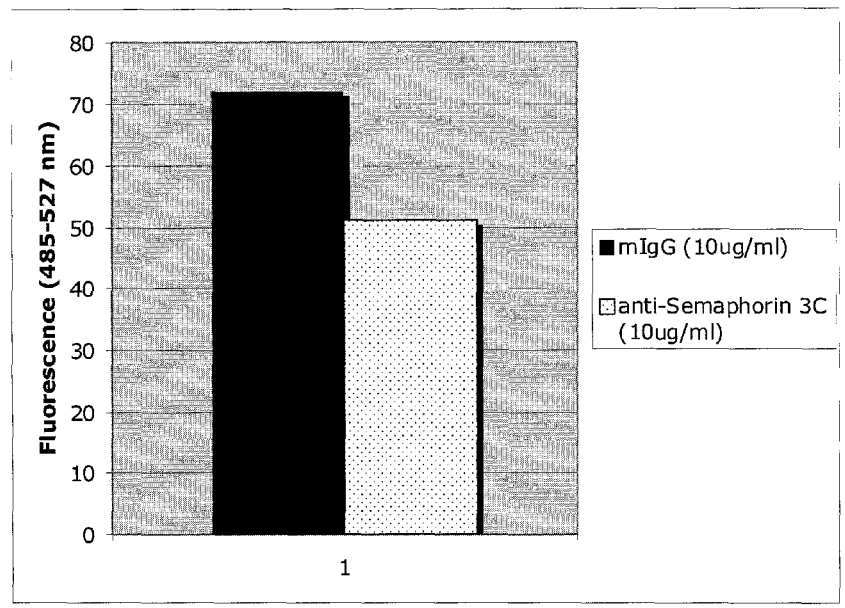
FIG. 16 shows a bar graph representing LNCaP cell proliferation, where the cells were treated with monoclonal anti-mouse Semaphorin 3C(R&D Diagnostics, MN), and anti-mouse IgGκ (Bethyl Laboratories, Montgomery, Tex.). Proliferation was monitored using the CyQuant proliferation assay kit (Invitrogen, Mississauga, ON) and data represents the Mean fluoresence 4 days following treatment.

LNCaP Cell Proliferation Inhibited by Anti-mouse SEMA3C Monoclonal Antibodies Treatment of LNCaP cells with a monoclonal antibody directed against SEMA3C suppressed LNCaP cell growth (FIG. 16). LNCaP cells were seeded at a density of 500 cells per well in 48-well tissue culture plates in growth medium (RPMI+10% FBS). Twenty-four hours later the growth medium was replaced with RPMI supplemented with 1% serum in the presence of 10 ug/ml anti-mouse Semaphorin 3C(R&D Diagnostics, MN), or anti-mouse IgGκ (Bethyl Laboratories, Montgomery, Tex.) antibody. Proliferation was monitored using the CyQuant proliferation assay kit (Invitrogen, Mississauga, ON). The cell growth was monitored at Day 4 using the CyQuant cell proliferation assay kit (Invitrogen, Mississauga, ON). Briefly the cells were harvested with trypsin, transferred to V-bottom 96-well plates and then centrifuged at 1400 RPM for 4 minutes. The supernatant was removed by gentle tapping and the cells were washed once with PBS. The cells were then centrifuged followed by removal of the wash buffer. The plates were immediately frozen at −80° C. for a minimum of 30 minutes prior to executing the CyQuant assay. Fluorescence was determined with excitation 485 nm and emission 527 nm in an Fluoroskan Ascent FL, (Thermo Labsystems, Helsinki, Finland).

The treatment of LNCaP cells with monoclonal anti-mouse SEMA3C showed a decrease in proliferation as compared to anti-mouse IgGκ (FIG. 16). The result suggests that antibodies to SEMA3C may be useful in the treatment of prostate cancer.

Although the foregoing invention has been described in some detail by way of illustration and example for purposes of clarity of understanding, it will be readily apparent to those of skill in the art in light of the teachings of this invention that changes and modification may be made thereto without departing from the spirit or scope of the appended claims.

References

Bruchovsky, N., P. Rennie, et al. (1988). Mechanisms and effects of androgen withdrawal therapies. *Prostatic Cancer: Rationale of endocrine management.* Berlin, Walter De Gruyer & Co.: 3-14.

Bruchovsky, N., P. S. Rennie, et al. (1989). Limitations of androgen withdrawal therapy of prostatic carcinoma—the next step? *Prostate Cancer—The Second Tokyo Symposium.* New York, Elsevier: 1-10.

Cardinale, A. and S. Biocca (2008). "The potential of intracellular antibodies for therapeutic targeting of protein-misfolding diseases." *Trends Mol Med* 14(9): 373-80.

Giordano, S., S. Corso, et al. (2002). "The semaphorin 4D receptor controls invasive growth by coupling with Met." *Nat Cell Biol* 4(9): 720-4.

Goldenberg, S. L., N. Bruchovsky, et al. (1988). "The combination of cyproterone acetate and low dose diethylstilbestrol in the treatment of advanced prostatic carcinoma." *J Urol* 140(6): 1460-5.

Heinlein, C. A. and Chang C. (2004), "Androgen Receptor in Prostate Cancer." *Endocrine Reviews* 25(2): 276-308.

Herman, J. G. and G. G. Meadows (2007). "Increased class 3 semaphorin expression modulates the invasive and adhesive properties of prostate cancer cells." *Int J Oncol* 30(5): 1231-8.

Hudson, P. J. and C. Souriau (2003). "Engineered antibodies." *Nat Med* 9(1): 129-34.

Huggins, C. and C. Hodges (1941). "Studies on prostatic cancer. I. the effect of castration, of estrogen and of androgen injection on serum phosphatases in metastatic carcinoma of the prostate." *Cancer Res* 1: 293-297.

Isaacs, J., O. Cussenot, et al. (1997). "Growth regulation of normal and malignant prostatic cells." *First International Consultation on Prostate Cancer:* 31-87.

Kolodkin, A. L., D. J. Matthes, et al. (1993). "The semaphorin genes encode a family of transmembrane and secreted growth cone guidance molecules." *Cell* 75(7): 1389-99.

Kruger, R. P., J. Aurandt, et al. (2005). "Semaphorins command cells to move." *Nat Rev Mol Cell Biol* 6(10): 789-800.

Lecerf, J. M., T. L. Shirley, et al. (2001). "Human single-chain Fv intrabodies counteract in situ huntingtin aggregation in cellular models of Huntington's disease." *Proc Natl Acad Sci USA* 98(8): 4764-9.

Negishi, M., I. Oinuma, and H. Katoh. 2005. Plexins: axon guidance and signal transduction. *Cell Mol Life Sci* 62:1363-1371.

Pan, W. H. and G. A. Clawson (2006). "Identifying accessible sites in RNA: the first step in designing antisense reagents." *Curr Med Chem* 13(25): 3083-103.

Patzel, V. (2007). "In silico selection of active siRNA." *Drug Discov Today* 12(3-4): 139-48.

Peek, A. S, and M. A. Behlke (2007). "Design of active small interfering RNAs." *Curr Opin Mol Ther* 9(2): 110-8.

Petrylak, D. P., C. M. Tangen, et al. (2004). "Docetaxel and estramustine compared with mitoxantrone and prednisone for advanced refractory prostate cancer." *N Engl J Med* 351(15): 1513-20.

Swiercz, J. M., R. Kuner, et al. (2004). "Plexin-B1/RhoGEF-mediated RhoA activation involves the receptor tyrosine kinase ErbB-2." *J Cell Biol* 165(6): 869-80.

Swiercz, J. M., T. Worzfeld, et al. (2008). "ErbB-2 and met reciprocally regulate cellular signaling via plexin-B1." *J Biol Chem* 283(4): 1893-901.

Tamagnone, L. and P. M. Comoglio (2000). "Signalling by semaphorin receptors: cell guidance and beyond." *Trends Cell Biol* 10(9): 377-83.

Tannock, I. F., R. de Wit, et al. (2004). "Docetaxel plus prednisone or mitoxantrone plus prednisone for advanced prostate cancer." *N Engl J Med* 351(15): 1502-12.

Verras, M., J. Lee, et al. (2007). "The androgen receptor negatively regulates the expression of c-Met: implications for a novel mechanism of prostate cancer progression." *Cancer Res* 67(3): 967-75.

---

INFORMAL SEQUENCE LISTING

SEQ ID NO: 1-Full length human SEMA3C-751 aa
MAFRTICVLVGVFICSICVKGSSQPQARVYLTFDELRETKTSEYFSLSHHPLDYRILLMDEDQDRIYVGSKD
HILSLNINNISQEALSVFWPASTIKVEECKMAGKDPTHGCGNFVRVIQTFNRTHLYVCGSGAFSPVCTYLNR
GRRSEDQVFMIDSKCESGKGRCSFNPNVNTVSVMINEELFSGMYIDFMGTDAAIFRSLTKRNAVRTDQHNSK
WLSEPMFVDAHVIPDGTDPNDAKVYFFFKEKLTDNNRSTKQIHSMIARICPNDTGGLRSLVNKWTTFLKARL
VCSVTDEDGPETHFDELEDVFLLETDNPRTTLVYGIFTTSSSVFKGSAVCVYHLSDIQTVFNGPFAHKEGPN
HQLISYQGRIPYPRPGTCPGGAFTPNMRTTKEFPDDVVTFIRNHPLMYNSIYPIHKRPLIVRIGTDYKYTKI
AVDRVNAADGRYHVLFLGTDRGTVQKVVVLPTNNSVSGELILEELEVFKNHAPITTMKISSKKQQLYVSSNE
GVSQVSLHRCHIYGTACADCCLARDPYCAWDGHSCSRFYPTGKRRSRRQDVRHGNPLTQCRGFNLKAYRNAA
EIVQYGVKNNTTFLECAPKSPQASIKWLLQKDKDRRKEVKLNERIIATSQGLLIRSVQGSDQGLYHCIATEN
SFKQTIAKINFKVLDSEMVAVVTDKWSPWTWASSVRALPFHPKDIMGAFSHSEMQMINQYCKDTRQQHQQGD
ESQKMRGDYGKLKALINSRKSRNRRNQLPES SEQ ID NO: 2-RNA interference compound capable of inhibiting SEMA3C
expression, 20 nt
5'-AUGGCAUUCCGGACAAUUUG-3'

SEQ ID NO: 3-Truncated human SEMA3C, comprising SEMA Domain-495 aa
MAFRTICVLVGVFICSICVKGSSQPQARVYLTFDELRETKTSEYFSLSHHPLDYRILLMDEDQDRIYVGSKD
HILSLNINNISQEALSVFWPASTIKVEECKMAGKDPTHGCGNFVRVIQTFNRTHLYVCGSGAFSPVCTYLNR
GRRSEDQVFMIDSKCESGKGRCSFNPNVNTVSVMINEELFSGMYIDFMGTDAAIFRSLTKRNAVRTDQHNSK
WLSEPMFVDAHVIPDGTDPNDAKVYFFFKEKLTDNNRSTKQIHSMIARICPNDTGGLRSLVNKWTTFLKARL
VCSVTDEDGPETHFDELEDVFLLETDNPRTTLVYGIFTTSSSVFKGSAVCVYHLSDIQTVFNGPFAHKEGPN
HQLISYQGRIPYPRPGTCPGGAFTPNMRTTKEFPDDVVTFIRNHPLMYNSIYPIHKRPLIVRIGTDYKYTKI
AVDRVNAADGRYHVLFLGTDRGTVQKVVVLPTNNSVSGELILEELEVFKNHAPITTMKISSKK SEQ ID NO: 4-SEMA3C (NM_006379 5189 bp mRNA) underlined and
bolded portion shows antisense RNA sequence (SEQ ID NO: 2)
      1 ggactgcgaa aggagcaggg ttgcggagct agggctccag cctgcggccg cgcattcttg
     61 cgtctggcca gccgcgagct ctaagggtcg gccccgcccg gtccgccccc gcggctccct
    121 gccaggctct cgcgggcgcg ctcggggtgg ggcctcgcgg ctggcggaga tgcggccggg
    181 gctgcgcggt ggtgatgcga gcctgctggg cggcgccgg gggcagccgg agccgcgcgc
    241 cgcggcgctg taatcggaca ccaagagcgc tcgccccgg cctccggcca ctttccattc
    301 actccgaggt gcttgattga gcgacgcgga gaagagctcc gggtgccgcg gcactgcagc
    361 gctgagattc ctttacaaag aaactcagag gaccgggaag aaagaatttc acctttgcga
    421 cgtgctagaa aataaggtcg tctgggaaaa ggactggaga cacaagcgca tccaacccg
    481 gtagcaaact gatgactttt ccgtgctgat ttctttcaac ctcggtattt tcccttggat -continued

| INFORMAL SEQUENCE LISTING |
| --- |
| 541 attaacttgc atatctgaag aaatggcatt ccggacaatt tgcgtgttgg ttggagtatt
601 tatttgttct atctgtgtga aaggatcttc ccagccccaa gcaagagttt atttaacatt
661 tgatgaactt cgagaaacca agacctctga atacttcagc ctttcccacc atcctttaga
721 ctacaggatt ttattaatgg atgaagatca ggaccggata tatgtgggaa gcaaagatca
781 cattctttcc ctgaatatta acaatataag tcaagaagct ttgagtgttt tctggccagc
841 atctacaatc aaagttgaag aatgcaaaat ggctggcaaa gatcccacac acggctgtgg
901 gaactttgtc cgtgtaattc agactttcaa tcgcacacat ttgtatgtct gtgggagtgg
961 cgctttcagt cctgtctgta cttacttgaa cagagggagg agatcagagg accaagtttt
1021 catgattgac tccaagtgtg aatctggaaa aggacgctgc tctttcaacc caacgtgaa
1081 cacggtgtct gttatgatca atgaggagct tttctctgga atgtatatag atttcatggg
1141 gacagatgct gctatttttc gaagtttaac caagaggaat gcggtcagaa ctgatcaaca
1201 taattccaaa tggctaagtg aacctatgtt tgtagatgca catgtcatcc cagatggtac
1261 tgatccaaat gatgctaagg tgtacttctt cttcaaagaa aaactgactg acaataacag
1321 gagcacgaaa cagattcatt ccatgattgc tcgaatatgt cctaatgaca ctggtggact
1381 gcgtagcctt gtcaacaagt ggaccacttt cttaaaggcg aggctggtgt gctcggtaac
1441 agatgaagac ggcccagaaa cacactttga tgaattagag gatgtgtttc tgctggaaac
1501 tgataacccg aggacaacac tagtgtatgg cattttttaca acatcaagct cagttttcaa
1561 aggatcagcc gtgtgtgtgt atcatttatc tgatatacag actgtgttta atgggccttt
1621 tgcccacaaa gaagggccca atcatcagct gatttcctat cagggcagaa ttccatatcc
1681 tcgccctgga acttgtccag gaggagcatt tacacccaat atgcgaacca ccaaggagtt
1741 cccagatgat gttgtcactt ttattcggaa ccatcctctc atgtacaatt ccatctaccc
1801 aatccacaaa aggcctttga ttgttcgtat tggcactgac tacaagtata caaagatagc
1861 tgtggatcga gtgaacgctg ctgatgggag ataccatgtc ctgtttctcg aacagatcg
1921 gggtactgtg caaaaagtgg ttgttcttcc tactaacaac tctgtcagtg gcgagctcat
1981 tctggaggag ctgaagtct ttaagaatca tgctcctata acaacaatga aaatttcatc
2041 taaaaagcaa cagttgtatg tgagttccaa tgaaggggtt tcccaggtat ctctgcaccg
2101 ctgccacatc tatggtacag cctgtgctga ctgctgcctg gcgcgggacc cttattgcgc
2161 ctgggatggc cattcctgtt ccagattcta cccaactggg aaacggagga gccgaagaca
2221 agatgtgaga catggaaacc cactgactca atgcagagga tttaatctaa aagcatacag
2281 aaatgcagct gaaattgtgc agtatggagt aaaaaataac accactttc tggagtgtgc
2341 ccccaagtct ccgcaggcat ctatcaagtg gctgttacag aaagacaaag acaggaggaa
2401 agaggttaag ctgaatgaac gaataatagc cacttcacag ggactcctga tccgctctgt
2461 tcagggttct gaccaaggac tttatcactg cattgctaca gaaaatagtt tcaagcagac
2521 catagccaag atcaacttca aagttttaga ttcagaaatg gtggctgttg tgacggacaa
2581 atggtcccca tggacctggg ccagctctgt gagggcttta cccttccacc cgaaggacat
2641 catgggggca ttcagccact cagaaatgca gatgattaac caatattgca aagacactcg
2701 gcagcaacat cagcagggag atgaatcaca gaaaatgaga ggggactatg caagttaaa
2761 ggccctcatc aatagtcgga aaagtagaaa caggaggaat cagttgccag agtcataata
2821 ttttcttatg tgggtcttat gcttccatta acaaatgctc tgtcttcaat gatcaaattt
2881 tgagcaaaga aacttgtgct ttaccaaggg gaattactga aaaaggtgat tactcctgaa
2941 gtgagtttta cacgaactga aatgagcatg catttttcttg tatgatagtg actagcacta
3001 gacatgtcat ggtcctcatg gtgcatataa atatatttaa cttaacccag attttattta
3061 tatctttatt caccttttct tcaaaatcga tatggtggct gcaaaactag aattgttgca
3121 tccctcaatt gaatgagggc catatccctg tggtattcct ttcctgcttt ggggcttag
3181 aattctaatt gtcagtgatt ttgtatatga aaacaagttc caaatccaca gcttttacgt
3241 agtaaaagtc ataaatgcat atgacagaat ggctatcaaa agaatagaa aaggaagacg
3301 gcatttaaag ttgtataaaa acacgagtta ttcataaaga gaaaatgatg agttttatg
3361 gttccaatga aatatgttgg ggttttttta agattgtaaa aataatcagt tactggtatc
3421 tgtcactgac ctttgtttcc ttattcagga agataaaaat cagtaaccta ccccatgaag
3481 atatttggtg ggagttatat cagtgaagca gtttggttta tattcttatg ttatcacctt
3541 ccaaacaaaa gcacttactt ttttttggaag ttatttattt tagactcaaa gaatataatc
3601 ttgcactact cagttattac tgtttgttct cttattccct agtctgtgtg gcaaattaaa
3661 caatataaga aggaaaaatt tgaagtatta gacttctaaa taagggtgtga aatcatcaga
3721 aagaaaaatc aaagtagaaa ctactaattt tttaagagga atttataaca aatatggcta
3781 gttttcaact tcagtactca aattcaatga ttcttccttt tattaaaacc agtctcagat
3841 atcatactga ttttttaagtc aacactatat atttttatgat cttttcagtg tgatggcaag
3901 gtgcttgtta tgtctagaaa gtaagaaaac aatatgagga gacattctgt ctttcaaaag
3961 gtaatggtac atacgttcac tggtctctaa gtgtaaaagt agtaaatttt gtgatgaata
4021 aaataattat ctcctaattg tatgttagaa taatttattt agaataattt catactgaaa
4081 ttattttctc caaataaaaa ttagatggaa aaatgtgaaa aaaattattc atgctctcat
4141 atatatttta aaaacactac ttttgctttt ttatttacct tttaagacat tttcatgctt
4201 ccaggtaaaa acagatattg taccatgtac ctaatccaaa tatcatataa acattttatt
4261 tatagttaat aatctatgat gaaggtaatt aaagtagatt atggcctttt taagtattgc
4321 agtctaaaac ttcaaaaact aaaatcattg tcaaaattaa tatgattatt aatcagaata
4381 tcagaatatg attcactatt taaactatga taattatga taatatatga ggaggcctcg
4441 ctatagcaaa aatagttaaa atgctgacat aacaccaaac ttcatttttt aaaaaatctg
4501 ttgttccaaa tgtgtataat tttaaagtaa tttctaaagc agtttattat aatggtttgc
4561 ctgcttaaaa ggtataatta aacttctttt ctcttctaca ttgacacaca gaaatgtgtc
4621 aatgtaaagc caaaaccatc ttctgtgttt atggccaatc tattctcaaa gttaaagta
4681 aaattgtttc agagtcacag ttcccttat ttcacataag cccaaactga tagacagtaa
4741 cggtgtttag ttttatacta tatttgtgct atttaattct ttctattttc acaattatta
4801 aattgtgtac acttcatta ctttttaaaaa tgtagaaatt cttcatgaac ataactctgc
4861 tgaatgtaaa agaaaatttt ttttcaaaaa tgctgttaat gtatactact ggtggttgat
4921 tggttttatt ttatgtagct tgacaattca gtgacttaat atctattcca tttgtattgt
4981 acataaaatt ttctagaaat acacttttttt ccaaagtgta agtttgtgaa tagattttag |

INFORMAL SEQUENCE LISTING

```
5041 catgatgaaa ctgtcataat ggtgaatgtt caatctgtgt aagaaaacaa actaaatgta
5101 gttgtcacac taaaatttaa ttggatattg atgaaatcat tggcctggca aaataaaaca
5161 tgttgaattc cccaaaaaaa aaaaaaaaa
```

TABLE 2

Gene walk antisense sequences for human SEMA3C aatattatgactctggcaac (SEQ ID NO: 5)
tgattcctcctgtttctact (SEQ ID NO: 6)
tttccgactattgatgaggg (SEQ ID NO: 7)
cctttaacttgccatagtcc (SEQ ID NO: 8)
cctctcatttctgtgattc (SEQ ID NO: 9)
atctccctgctgatgttgct (SEQ ID NO: 10)
gccgagtgtctttgcaatat (SEQ ID NO: 11)
tggttaatcatctgcatttc (SEQ ID NO: 12)
tgagtggctgaatgccccca (SEQ ID NO: 13)
tgatgtccttcgggtggaag (SEQ ID NO: 14)
ggtaaagccctcacagagct (SEQ ID NO: 15)
ggcccaggtccatggggacc (SEQ ID NO: 16)
atttgtccgtcacaacagcc (SEQ ID NO: 17)
accatttctgaatctaaaac (SEQ ID NO: 18)
tttgaagttgatcttggcta (SEQ ID NO: 19)
tggtctgcttgaaactattt (SEQ ID NO: 20)
tctgtagcaatgcagtgata (SEQ ID NO: 21)
aagtccttggtcagaaccct (SEQ ID NO: 22)
gaacagagcggatcaggagt (SEQ ID NO: 23)
ccctgtgaagtggctattat (SEQ ID NO: 24)
tcgttcattcagcttaacct (SEQ ID NO: 25)
ctttcctcctgtctttgtct (SEQ ID NO: 26)
ttctgtaacagccacttgat (SEQ ID NO: 27)
agatgcctgcggagacttgg (SEQ ID NO: 28)
gggcacactccagaaaagtg (SEQ ID NO: 29)
gtgttattttttactccata (SEQ ID NO: 30)
ctgcacaatttcagctgcat (SEQ ID NO: 31)
ttctgtatgctttagatta (SEQ ID NO: 32)
aatcctctgcattgagtcag (SEQ ID NO: 33)
tgggtttcatgtctcacat (SEQ ID NO: 34)
cttgtcttcggctcctccgt (SEQ ID NO: 35)
ttcccagttgggtagaatct (SEQ ID NO: 36)
ggaacaggaatggccatccc (SEQ ID NO: 37)
aggcgcaataagggtcccgc (SEQ ID NO: 38)

TABLE 2-continued

Gene walk antisense sequences for human SEMA3C gccaggcagcagtcagcaca (SEQ ID NO: 39)
ggctgtaccatagatgtggc (SEQ ID NO: 40)
agcggtgcagagatacctgg (SEQ ID NO: 41)
gaaacccttcattggaact (SEQ ID NO: 42)
cacatacaactgttgctttt (SEQ ID NO: 43)
tagatgaaattttcattgtt (SEQ ID NO: 44)
gttataggagcatgattctt (SEQ ID NO: 45)
aaagacttccagctcctcca (SEQ ID NO: 46)
gaatgagctcgccactgaca (SEQ ID NO: 47)
gagttgttagtaggaagaac (SEQ ID NO: 48)
aaccacttttgcacagtac (SEQ ID NO: 49)
cccgatctgttccgagaaac (SEQ ID NO: 50)
aggacatggtatctcccatc (SEQ ID NO: 51)
agcagcgttcactcgatcca (SEQ ID NO: 52)
cagctatctttgtatacttg (SEQ ID NO: 53)
tagtcagtgccaatacgaac (SEQ ID NO: 54)
aatcaaaggccttttgtgga (SEQ ID NO: 55)
ttgggtagatggaattgtac (SEQ ID NO: 56)
atgagaggatggttccgaat (SEQ ID NO: 57)
aaaagtgacaacatcatctg (SEQ ID NO: 58)
ggaactccttggtggttcgc (SEQ ID NO: 59)
atattgggtgtaaatgctcc (SEQ ID NO: 60)
tcctggacaagttccagggc (SEQ ID NO: 61)
gaggatatggaattctgccc (SEQ ID NO: 62)
tgataggaaatcagctgatg (SEQ ID NO: 63)
attgggcccttctttgtggg (SEQ ID NO: 64)
caaaaggcccattaaacaca (SEQ ID NO: 65)
gtctgtatatcagataaatg (SEQ ID NO: 66)
atacacacacacggctgatc (SEQ ID NO: 67)
ctttgaaaactgagcttgat (SEQ ID NO: 68)
gttgtaaaaatgccatacac (SEQ ID NO: 69)
tagtgttgtcctcgggttat (SEQ ID NO: 70)
cagtttccagcagaaacaca (SEQ ID NO: 71)

TABLE 2-continued

Gene walk antisense sequences for human SEMA3C tcctctaattcatcaaagtg (SEQ ID NO: 72)

tgtttctgggccgtcttcat (SEQ ID NO: 73)

ctgttaccgagcacaccagc (SEQ ID NO: 74)

ctcgcctttaagaaagtggt (SEQ ID NO: 75)

ccacttgttgacaaggctac (SEQ ID NO: 76)

gcagtccaccagtgtcatta (SEQ ID NO: 77)

ggacatattcgagcaatcat (SEQ ID NO: 78)

ggaatgaatctgtttcgtgc (SEQ ID NO: 79)

tcctgttattgtcagtcagt (SEQ ID NO: 80)

ttttctttgaagaagaagta (SEQ ID NO: 81)

caccttagcatcatttggat (SEQ ID NO: 82)

cagtaccatctgggatgaca (SEQ ID NO: 83)

tgtgcatctacaaacatagg (SEQ ID NO: 84)

ttcacttagccatttggaat (SEQ ID NO: 85)

tatgttgatcagttctgacc (SEQ ID NO: 86)

gcattcctcttggttaaact (SEQ ID NO: 87)

tcgaaaaatagcagcatctg (SEQ ID NO: 88)

tccccatgaaatctatatac (SEQ ID NO: 89)

attccagagaaaagctcctc (SEQ ID NO: 90)

attgatcataacagacaccg (SEQ ID NO: 91)

tgttcacgttggggttgaaa (SEQ ID NO: 92)

gagcagcgtccttttccaga (SEQ ID NO: 93)

ttcacacttggagtcaatca (SEQ ID NO: 94)

tgaaaacttggtcctctgat (SEQ ID NO: 95)

TABLE 2-continued

Gene walk antisense sequences for human SEMA3C ctcctccctctgttcaagta (SEQ ID NO: 96)

agtacagacaggactgaaag (SEQ ID NO: 97)

cgccactcccacagacatac (SEQ ID NO: 98)

aaatgtgtgcgattgaaagt (SEQ ID NO: 99)

ctgaattacacggacaaagt (SEQ ID NO: 100)

tcccacagccgtgtgtggga (SEQ ID NO: 101)

tctttgccagccatttttgca (SEQ ID NO: 102)

ttcttcaactttgattgtag (SEQ ID NO: 103)

atgctggccagaaaacactc (SEQ ID NO: 104)

aaagcttcttgacttatatt (SEQ ID NO: 105)

gttaatattcagggaaagaa (SEQ ID NO: 106)

tgtgatctttgcttcccaca (SEQ ID NO: 107)

tatatccggtcctgatcttc (SEQ ID NO: 108)

atccattaataaaatcctgt (SEQ ID NO: 109)

agtctaaaggatggtgggaa (SEQ ID NO: 110)

aggctgaagtattcagaggt (SEQ ID NO: 111)

cttggtttctcgaagttcat (SEQ ID NO: 112)

caaatgttaaataaactctt (SEQ ID NO: 113)

gcttggggctgggaagatcc (SEQ ID NO: 114)

tttcacacagatagaacaaa (SEQ ID NO: 115)

taaatactccaaccaacacg (SEQ ID NO: 116)

caaattgtccggaatgccat (SEQ ID NO: 117)

cttttgccagccatttttgcat (SEQ ID NO: 118)

tacctgggaaaccccttcat (SEQ ID NO: 119)

---

The invention claimed is:

1. A method for treating prostate cancer in a subject, the method comprising:
   administering to the subject a therapeutically effective amount of an anti-SEMA3C antibody having SEMA3C inhibitory activity.

2. The method of claim 1, wherein said prostate cancer is androgen-dependent.

3. The method of claim 1, wherein the prostate cancer is an androgen receptor (AR) positive prostate cancer.

4. The method of claim 1, wherein the anti-SEMA3C antibody is selected from one or more of the following: a polyclonal antibody; a monoclonal antibody; an antigen binding fragment of an antibody; or a single chain antibody.

5. The method of claim 1 further comprising administering androgen deprivation therapy.

6. The method of claim 5, wherein the androgen deprivation therapy and the anti-SEMA3C antibody having SEMA3C inhibitory activity are initiated at about the same time.

7. The method of claim 5, wherein the anti-SEMA3C antibody having SEMA3C inhibitory activity is initiated after the androgen deprivation therapy and before the prostate cancer becomes androgen independent.

8. The method of claim 5, wherein the anti-SEMA3C antibody is selected from one or more of the following: a polyclonal antibody; a monoclonal antibody; an antigen binding fragment of an antibody; or a single chain antibody.

9. The method of claim 5, wherein the androgen deprivation therapy comprises administering a luteinizing hormone-releasing hormone (LHRH) analog.

10. The method of claim 5, wherein the androgen deprivation therapy comprises administering anti-androgen treatment.

11. The method of claim 5, wherein the androgen deprivation therapy comprises administering an adrenal androgen inhibitor.

12. The method of claim 5, wherein the androgen deprivation therapy is surgical.

13. The method of claim 5, wherein the androgen deprivation therapy and the anti-SEMA3C antibody having SEMA3C inhibitory activity are administered with one or more further therapeutic regimen(s).

14. The method of claim 13, wherein the therapeutic regimen is a chemotherapeutic regimen.

15. The method of claim 13, wherein the therapeutic regimen is a radiotherapeutic regimen.

* * * * *